US011617546B2

(12) United States Patent
Zizi et al.

(10) Patent No.: US 11,617,546 B2
(45) Date of Patent: *Apr. 4, 2023

(54) MONITORING FOR HEALTH CHANGES OF A USER BASED ON NEURO AND NEURO-MECHANICAL MOTION

(71) Applicant: Aerendir Mobile Inc., Mountain View, CA (US)

(72) Inventors: Martin Zizi, Brussels (BE); Hugh Sharkey, Redwood City, CA (US)

(73) Assignee: Proprius Technolgies S.A.R.L, Luxembourg (LU)

( * ) Notice: Subject to any disclaimer, the term of this patent is extended or adjusted under 35 U.S.C. 154(b) by 247 days.

This patent is subject to a terminal disclaimer.

(21) Appl. No.: 16/436,891

(22) Filed: Jun. 10, 2019

(65) Prior Publication Data

US 2020/0100732 A1    Apr. 2, 2020

Related U.S. Application Data

(63) Continuation of application No. 15/013,764, filed on Feb. 2, 2016, now Pat. No. 10,357,210.

(Continued)

(51) Int. Cl.
*A61B 5/00* (2006.01)
*A61B 5/11* (2006.01)
(Continued)

(52) U.S. Cl.
CPC .......... *A61B 5/7475* (2013.01); *A61B 5/1101* (2013.01); *A61B 5/117* (2013.01);
(Continued)

(58) Field of Classification Search
CPC ................ A61B 5/7475; A61B 5/4842; A61B 5/7275; A61B 5/7235; A61B 5/7253;
(Continued)

(56) References Cited

U.S. PATENT DOCUMENTS

| | | | | |
|---|---|---|---|---|
| 3,972,038 A * | 7/1976 | Fletcher | ............... | A61B 5/0002 340/870.18 |
| 5,197,489 A * | 3/1993 | Conlan | .................... | A61B 5/11 600/484 |
| 5,293,879 A * | 3/1994 | Vonk | .................... | A61B 5/1101 600/595 |
| 5,573,011 A * | 11/1996 | Felsing | ................ | A61B 5/1101 600/595 |
| 6,454,706 B1 * | 9/2002 | Pullman | ............... | A61B 5/4082 600/300 |
| 7,236,156 B2 * | 6/2007 | Liberty | ................ | A61B 5/1101 345/156 |

(Continued)

*Primary Examiner* — Eugene T Wu
(74) *Attorney, Agent, or Firm* — Alford Law Group, Inc.

(57) ABSTRACT

In accordance with one embodiment, a method for determining changes in health of a user is disclosed. The method includes sensing multi-dimensional motion of a body part of a user to generate a first multi-dimensional motion signal at a first time and date; in response to the first multi-dimensional motion signal, generating a first neuro-mechanical fingerprint; generating a first health measure in response to the first NFP and user calibration parameters; sensing multi-dimensional motion of the body part of the user to generate another multi-dimensional motion signal at another time and date; in response to the another multi-dimensional motion signal, generating another neuro-mechanical fingerprint; generating another health measure in response to the another NFP and the user calibration parameters; and comparing the first health measure with the another health measure to determine a difference representing the health degradation of the user.

18 Claims, 24 Drawing Sheets

Related U.S. Application Data

(60) Provisional application No. 62/112,153, filed on Feb. 4, 2015.

(51) Int. Cl.
*A61B 5/117* (2016.01)
*A61B 5/18* (2006.01)

(52) U.S. Cl.
CPC .......... *A61B 5/4064* (2013.01); *A61B 5/4842* (2013.01); *A61B 5/7235* (2013.01); *A61B 5/7253* (2013.01); *A61B 5/7275* (2013.01); *A61B 5/18* (2013.01); *A61B 5/4088* (2013.01); *A61B 5/6897* (2013.01); *A61B 5/6898* (2013.01)

(58) Field of Classification Search
CPC ..... A61B 5/1101; A61B 5/117; A61B 5/4064; A61B 5/18; A61B 5/6897; A61B 5/4088; A61B 5/6898
See application file for complete search history.

(56) References Cited

U.S. PATENT DOCUMENTS

| | | | |
|---|---|---|---|
| 2003/0216656 A1* | 11/2003 | Berme | A61B 5/318 600/509 |
| 2005/0243061 A1* | 11/2005 | Liberty | A61B 5/1101 345/158 |
| 2010/0056878 A1* | 3/2010 | Partin | A61B 5/0002 600/301 |
| 2010/0145236 A1* | 6/2010 | Greenberg | A61B 5/1101 600/595 |
| 2013/0041290 A1* | 2/2013 | Kording | A61B 5/1101 600/595 |
| 2013/0338539 A1* | 12/2013 | Bailey | A61B 5/1101 600/595 |
| 2013/0339908 A1* | 12/2013 | Bailey | G06F 3/017 715/863 |
| 2014/0073994 A1* | 3/2014 | Machado | A61B 5/6897 600/595 |
| 2014/0171834 A1* | 6/2014 | DeGoede | A61B 5/1124 600/595 |
| 2014/0343462 A1* | 11/2014 | Burnet | A61B 5/1101 600/595 |

* cited by examiner (Background)**
Categories of Identification Methods

Remote Authentication

Local Authentication

FIG. 4
Multi Factor Authentication combines two or more different elements

| Biometrics | Permanence | Collectability | Performance | Acceptability | Circumvention | Uniqueness | Universality | Relative |
|---|---|---|---|---|---|---|---|---|
| Keystroke Dynamics | L | M | L | M | M | L | L | - - |
| Voice | L | M | L | H | L | L | M | - |
| Signature | L | H | L | H | L | L | L | + |
| Face | M | H | L | H | L | L | H | + |
| Hand Geometry | M | H | M | M | M | M | M | ++ |
| Hand Vein | M | M | M | M | H | M | M | ++ |
| DNA | H | L | H | L | L | H | H | ++ |
| Retina | M | L | H | L | H | H | H | +++ |
| Facial Thermogram | L | H | M | H | H | H | H | +++ |
| Fingerprint | H | M | H | M | H | H | M | +++ |
| Iris | H | M | H | L | H | H | H | +++ |
| *N F Ps* | H | H | H | H | H | H | H | ++++ |

H = High   M = Medium   L = Low

FIG. 5
Comparative matrix of biometric identification technologies

Properties of several basic tremor types

| Tremor type | Frequency (in Hz) | Activation condition |  |  |
|---|---|---|---|---|
|  |  | Resting | Postural | Kinetic |
| Parkinsonian | 3-7 | X | Z | X |
| Essential | 4-12 |  | X | X |
| Orthostatic | 13-18 |  | X |  |
| Physiological | 3-30 |  | X |  |
| Enhanced physiological | 8-12 |  | X |  |
| Cerebellar | 3-5 |  | Z | X |
| Dystonic | 4-7 |  | X | X |
| Holmes' | <4.5 | X |  | X |
| Neuropathic | 4-7 |  | X |  |
| Palatal | <7 | X |  |  |
| Psychogenic | 4-7 |  | X |  |
| Task-specific | 5-7 |  |  | X |
| X - characteristic condition; Z - occurs in some | | | | |

FIG. 6

EIGENVECTOR

MONITORING FOR HEALTH CHANGES OF A USER BASED ON NEURO AND NEURO-MECHANICAL MOTION

CROSS REFERENCE TO RELATED APPLICATIONS

This United States (U.S.) patent application claims the benefit of U.S. patent application Ser. No. 15/013,764 titled DETERMINING HEALTH CHANGE OF A USER WITH NEURO AND NEURO-MECHANICAL FINGERPRINTS filed on Feb. 2, 2016 by inventors Martin Zizi et al. application Ser. No. 15/013,764 claims the benefit of U.S. Patent Application No. 62/112,153 entitled LOCAL USER AUTHENTICATION WITH NEURO-MECHANICAL FINGERPRINTS filed on Feb. 4, 2015 by inventors Martin Zizi et al.

FIELD

The embodiments relate generally to health analysis and diagnosis of a user.

BACKGROUND

Wide area network connections over the Internet have interconnected many electronic devices, such as computers and mobile smart phones, to remote servers and remote storage devices so that cloud computer services can be provided. More electronic devices are poised to be interconnected over the Internet as wireless radio transmitter/receivers are added to them.

Access by a user to some electronic devices and databases is often by a login name and password. As more portable electronic devices are used, such as laptop computers and mobile smart phones, in a highly mobile computing environment, correct authentication of people and devices becomes important to ascertain authorized use and lower risks linked to data misrouting. For example, as more mobile health electronic devices are introduced, privacy of the captured health data by the mobile health devices becomes important. As more banking and payments are made using mobile electronic devices, authorized use becomes important.

Authentication of a user using a local electronic device is often performed by a remote server. Software applications executed by the local electronic device often save the login name and password of the user to make an electronic device and its software applications easier to use. Protecting the local access of the user's electronic device has become more important in protecting the user and his/her login name and password when an electronic device is lost or stolen. With electronic devices now being used to make payments like credit card transactions, protection of local access to a user's electronic device has become even more important.

Referring now to FIG. 1, various known behavioral and anatomical identification methods are illustrated. Behavioral identification methods are linked to what the user does or his/her habits. Known anatomical identification methods are linked to physical features of the user, such as fingerprints, iris eye scans, veins, facial scans, and DNA.

Biometrics are being used to better authenticate a user to provide greater protection of mobile electronic devices. Biometrics have been pursued with anatomical based approaches (i.e., physical features such as fingerprints, iris eye scans, veins, facial scans, DNA, etc.) and habit (behavioral) approaches (typing or keystrokes, handwriting signatures, voice or vocal inflections). For example, an anatomical aspect of the user, such as a fingerprint, is used to locally authenticate a user and restrict access to the electronic device. As another example, hand morphology or the position of the veins can be used with an image analysis to locally authenticate a user and restrict access to the electronic device.

Behavioral aspects of a user may also be used to better authenticate a user to provide greater protection of mobile electronic devices. The behavioral aspect involves a personal profile of a user's unique habits, tastes, and behavior. For example, the way a user signs his/her signature is a unique behavioral aspect that can be used to verify a user's identity.

However, neither known anatomical nor known behavioral aspects of user identification are foolproof. For example, known user data used for comparison can be stolen from a server and used without the user's knowledge. Additional hardware is often required to capture biometrics from the user that leads to increased costs. With known added hardware, risks may be increased where a user may be forced by another to unwillingly capture biometric data. Behavioral aspects may be somewhat intrusive and raise privacy issues. Sensing for behavioral aspects is often performed with software that requires a system to remain powered on, consuming energy that is often stored in rechargeable batteries. Moreover, biometrics using behavioral aspects often require the added expense of maintaining remote centralized databases.

BRIEF SUMMARY

Using biometrics with known anatomical and/or known behavior aspects of a user for identification have some disadvantages.

There is a need for a user authentication solution that is easy to use, de-centralized so it can be used locally, is substantially fail-safe from predators, consumes low power for battery applications, and respects a user's privacy by protecting a user's data so that it is readily adoptable.

The user authentication solution disclosed herein provides fail-safe authentications in a decentralized mobile environment while protecting a user's privacy and data. The user authentication solution disclosed herein employs a different form of biometric that is tamper resistant.

The user authentication solution disclosed herein can employ 3-D sensors and signal processing to capture signals ("micro-motion signals") that represent neuro-muscular micro-functions of a user, that are translated into well defined micro-motions. Signal processing algorithms and feature extraction are then used to capture unique signal features in the micro-motion signals. These unique signal features associated with the neuro-muscular micro-motions of a user, can be used to uniquely identify a user, somewhat similar to a fingerprint. Accordingly, these unique signal features associated with the neuro-muscular micro-motions of a user are referred to herein as "neuro-mechanical fingerprints" (NFPs). The neuro-mechanical fingerprints can be used for local user authentication at a mobile electronic device, such as a laptop computer or smartphone, or at other types of electronic devices. Using the NFP of a user, captured by sensors and extracted by algorithms, avoids profiling and storing a user's habits or patterned behavior.

The embodiments of the user authentication solution employing sensors and signal processing algorithms to generate and regenerate neuro-mechanical fingerprints (NFPs)

of an authorized user are disclosed by the attached figures and the detailed description herein.

BRIEF DESCRIPTIONS OF THE DRAWINGS

FIG. 4 is a chart illustrating authentication techniques that may be used with NFP authentication to provide multi-factor authentication.

FIG. 5 is a chart to compare various biometric identification techniques against NFP authentication.

FIG. 6 is a table of tremor types and associated frequencies and conditions.

DETAILED DESCRIPTION

Figure 1:
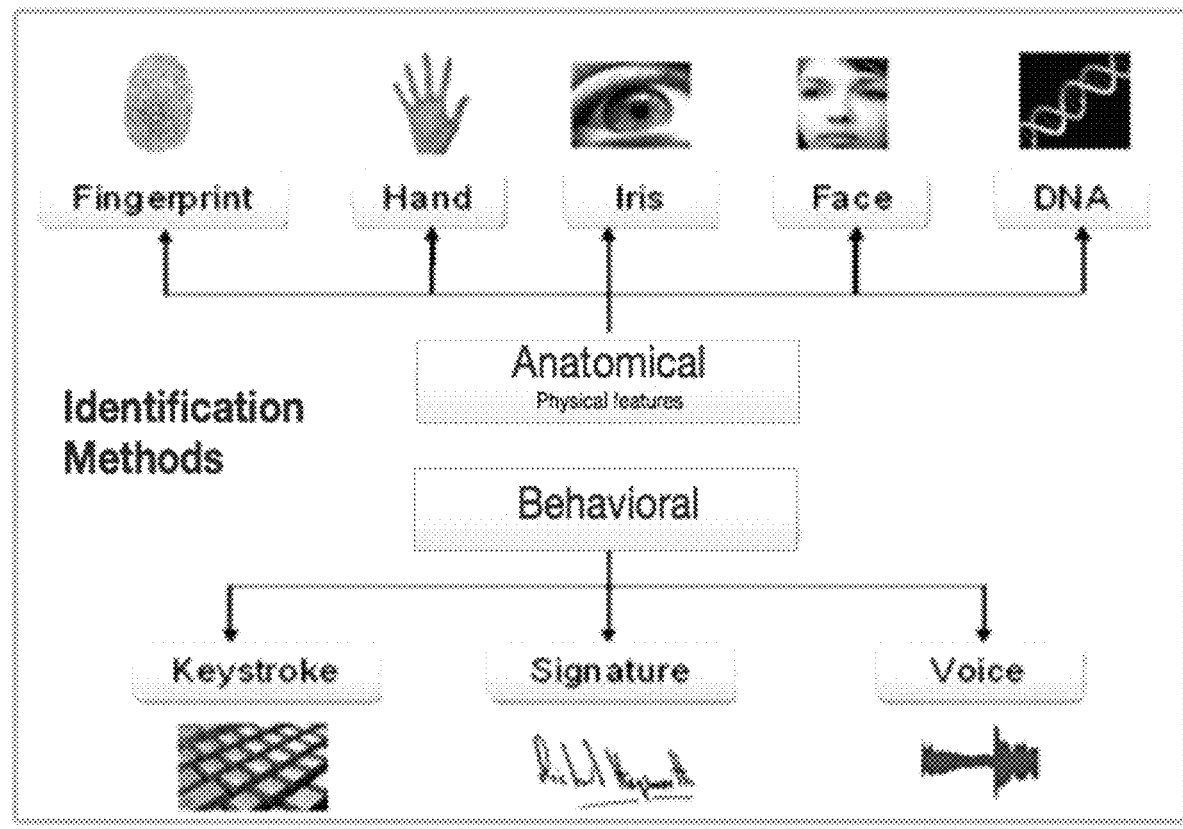
FIG. 1 is a background figure illustrating various behavioral and physiological identification methods.

In the following detailed description of the embodiments, numerous specific details are set forth in order to provide a thorough understanding. However, it will be obvious to one skilled in the art that the embodiments may be practiced without these specific details. In other instances well known methods, procedures, components, and circuits have not been described in detail so as not to unnecessarily obscure aspects of the embodiments.

The embodiments include methods, apparatus, and systems for forming and utilizing neuro-mechanical fingerprints (NFPs) to identify and authenticate a user.
Introduction Certain user motions are habitual or part of a user's motion repertoire. A user signing a document, for example, is a contextual motion that a user develops with behavioral habits. The motions usually analyzed of a signed signature are the macro-motions or large scale motions that a user makes with a writing instrument. For example, from the large motions of a signed signature one may determine with ones eyes whether the writer was left handed or right handed, for example.

While these large motions may be useful, there are also micro-motions (very small motions) that a user makes when signing, making other motions, or simply at rest making no motion. These micro-motions are neuro-derived or neuro-based and invisible to the eyes. These micro-motions of a user are due to the unique neuromuscular anatomy of each human being and may be also referred to herein as neuro-derived micro-motions. These micro-motions are also linked to the motor control processes from the motor cortex of an individual down to his/her hands. With one or more sensors, signal processing algorithms, and/or filters, electronic signals ("motion signals" and "micro-motions signals") can be captured that include the neuro-derived micro-motions of a user. Of specific interest are micro-motion electronic signals that represent the micro-motions of the user within the motion signals.

Micro-motions of a user are linked to the cortical and subcortical control of the motor activities in the brain or elsewhere in the nervous system of a human body. Like a mechanical filter, the specific musculoskeletal anatomy of an individual can affect the micro-motions of a user and contribute to the motion signals that include the micro-motions of a user. The motion signals captured from a user can also reflect part of the proprioceptive control loops that include the brain and proprioceptors that are present in a user's human body.

When motion signals are analyzed appropriately for micro-motion signals representing micro-motions of users, the resulting data can yield unique and stable physiological identifiers, more specifically neurological identifiers, that can be used as unwritten signatures. These unique identifiers are a user's neuro-mechanical fingerprints. Neuro-mechanical fingerprints may also be referred to herein as NeuroFingerPrints (NFPs).

The motions of a user, including a user's macro-motions and a user's micro-motions, can be captured by various electronic sensors. For example, an electronic touch sensor or an electronic accelerometer may be used to capture the macro and micro motions of a user. U.S. patent application Ser. No. 13/823,107 filed by Geoff Klein on Jan. 5, 2012, incorporated herein by reference, describes how an accelerometer may be used to unobtrusively capture motion data of a user over time when operating an electronic device and generate a motion-repertoire that can be used to recognize a user. U.S. patent application Ser. No. 13/823,107 makes use of repertoires or motion habits. The embodiments disclosed herein do not build nor rely on motion repertoires. The embodiments disclosed herein extract signals linked to quality control mechanisms of the nervous system. U.S. patent application Ser. No. 13/823,107 ignores those user's neuro-derived micro-motions that are of interest to the embodiments disclosed herein. Moreover, in the generation of neuro-mechanical fingerprints, the macro-motion signals are suppressed or filtered out to capture the micro-motions signal component. When using a three-dimensional accelerometer to capture a user's micro-motions, the macro-motions signal needs filtering out from the micro-motion signal data. The vector due to the force of gravity is also ignored in U.S. patent application Ser. No. 13/823,107. When using a three-dimensional accelerometer, the force of gravity is compensated for or filtered out in the generation of the micro-motions signal.

Referring now to FIGS. 2A-2D, examples of three-dimensional Poincare' phase plot diagrams for four different users are shown. Each three-dimensional Poincare' phase plot diagram shows a pattern 200A-200D of gravity corrected three-dimensional accelerometry data.

The raw accelerometry data was obtained over the same period of time with users doing macro-motions with their hands using the same electronic device. The electronic device has three-dimensional accelerometer sensors to capture raw accelerometry data in the three dimensions of X, Y, and Z.

Signal processing is performed on the raw accelerometry data to filter or suppress unwanted signals, correct for gravity and extract the signals (micro-motion signals) that represent the neuro-derived micro-motions of a user's hand or finger. The three dimensions of micro-motion signals $x(t)$, $y(t)$, $z(t)$ over the sample period of time for a user can be further processed into phase(t), $y(t)$, $z(t)$ and plotted in a three-dimensional Poincare' phase plot diagram. If the sample period of time is short, the motion signals $x(t)$, $y(t)$, $z(t)$ sensed from a sample of the neuro-muscular micro-motions of the user may be stored into a storage device in digital form to represent a neuro-mechanical fingerprint (NFP). The digital form of the micro-motions signals may be encrypted with an encryption algorithm and an encryption key prior to storage in order to protect it from unauthorized access by unauthorized persons.

Figure 2A:
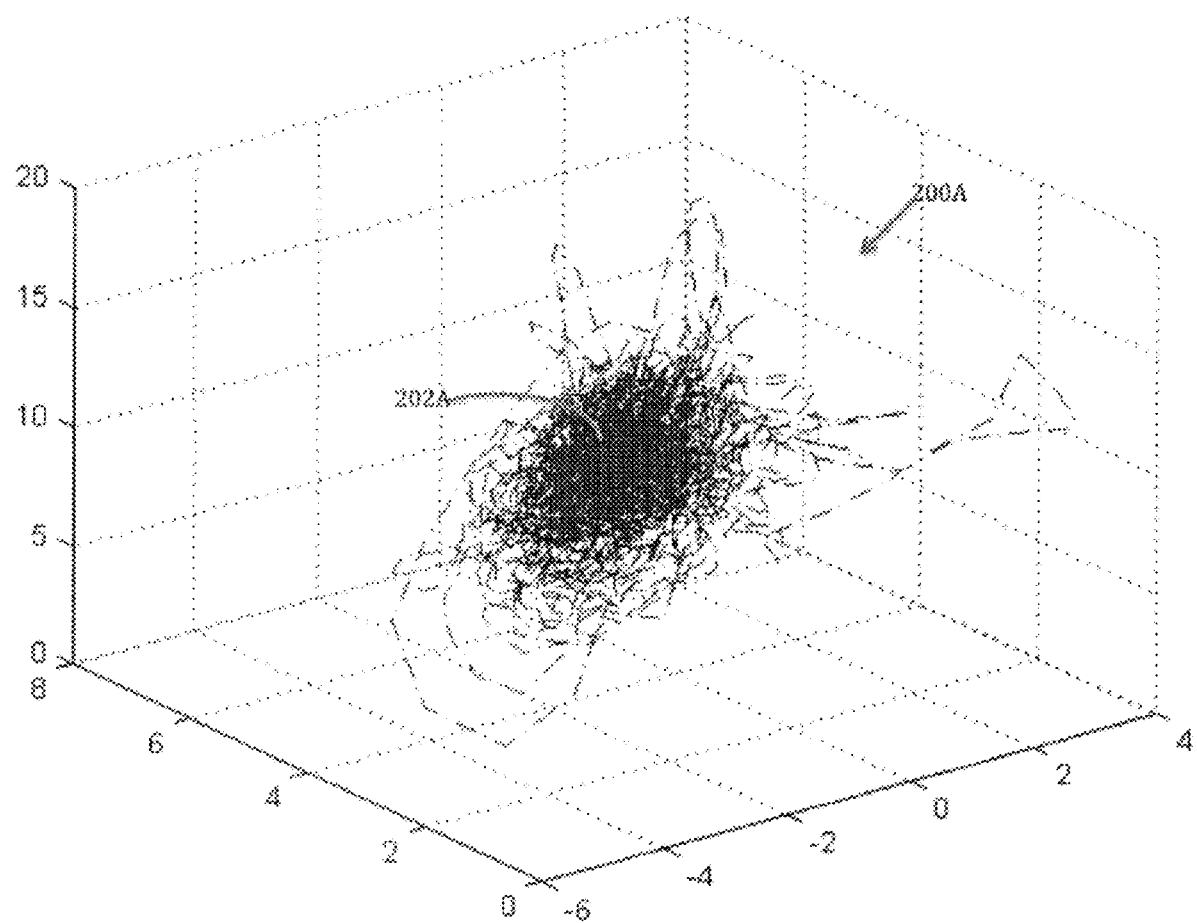
FIGS. 2A-2D illustrate examples of Poincare' phase plot diagrams showing gravity corrected three-dimensional accelerometry data captured from different users.
Figure 2B:
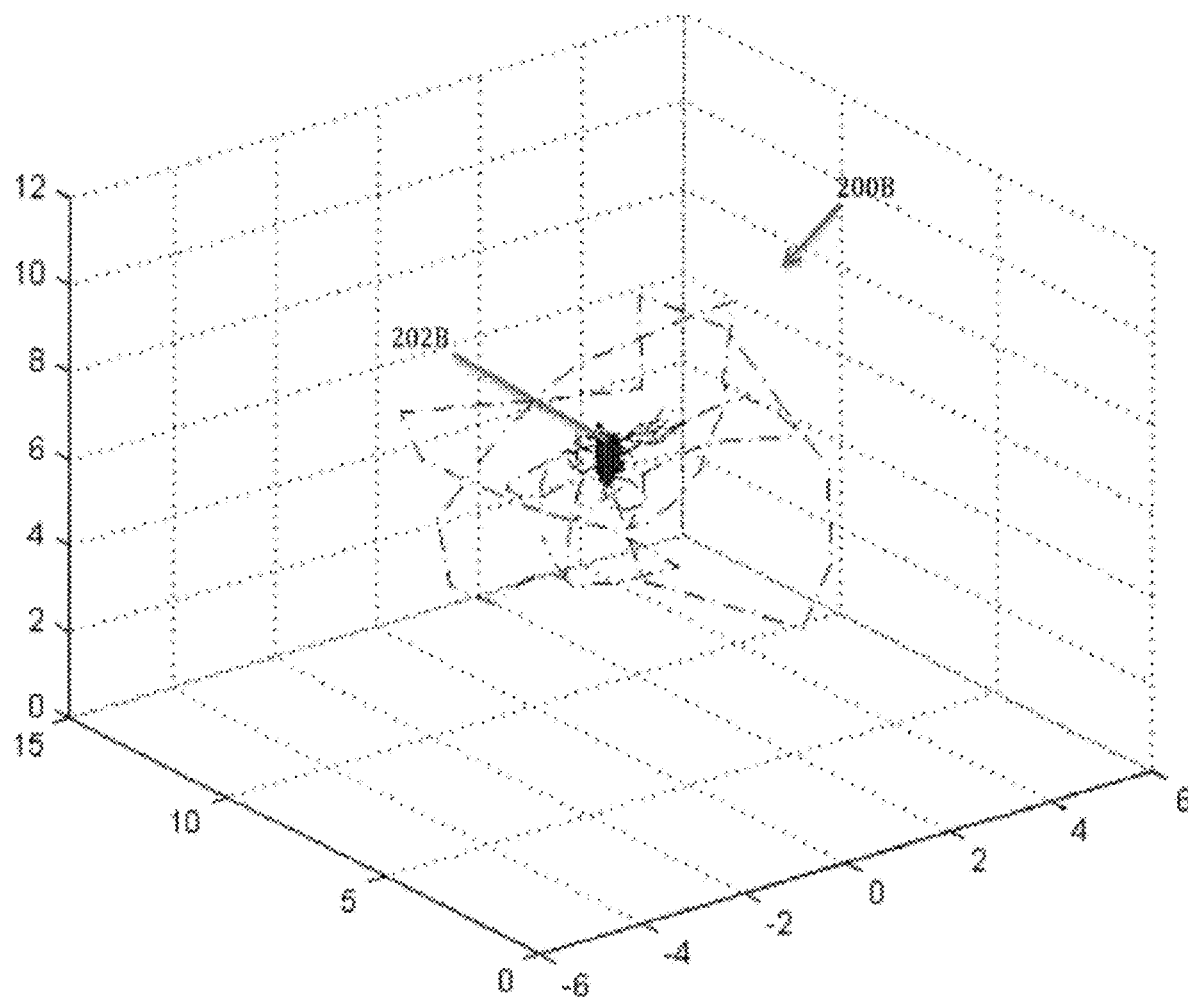
Figure 2C:
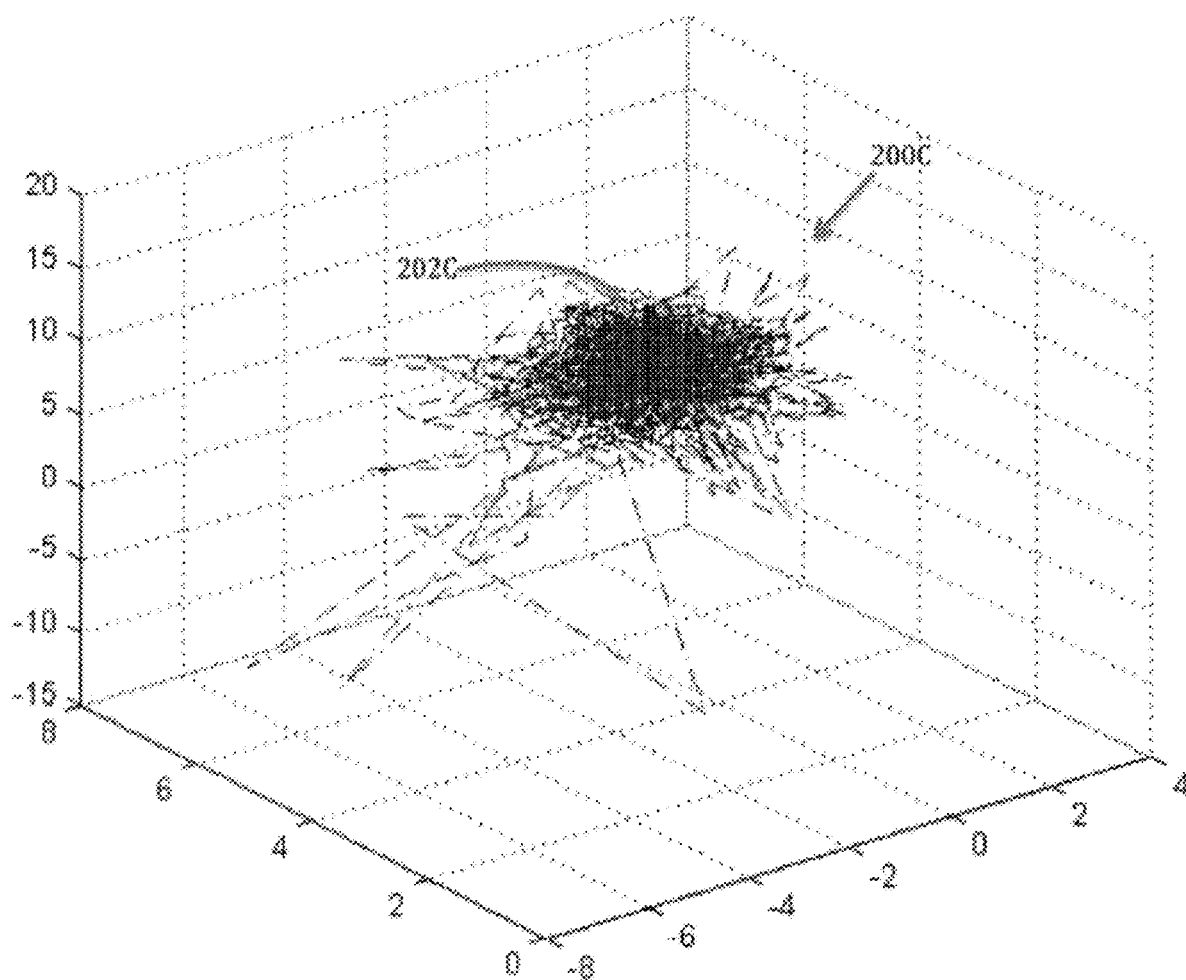
Figure 2D:
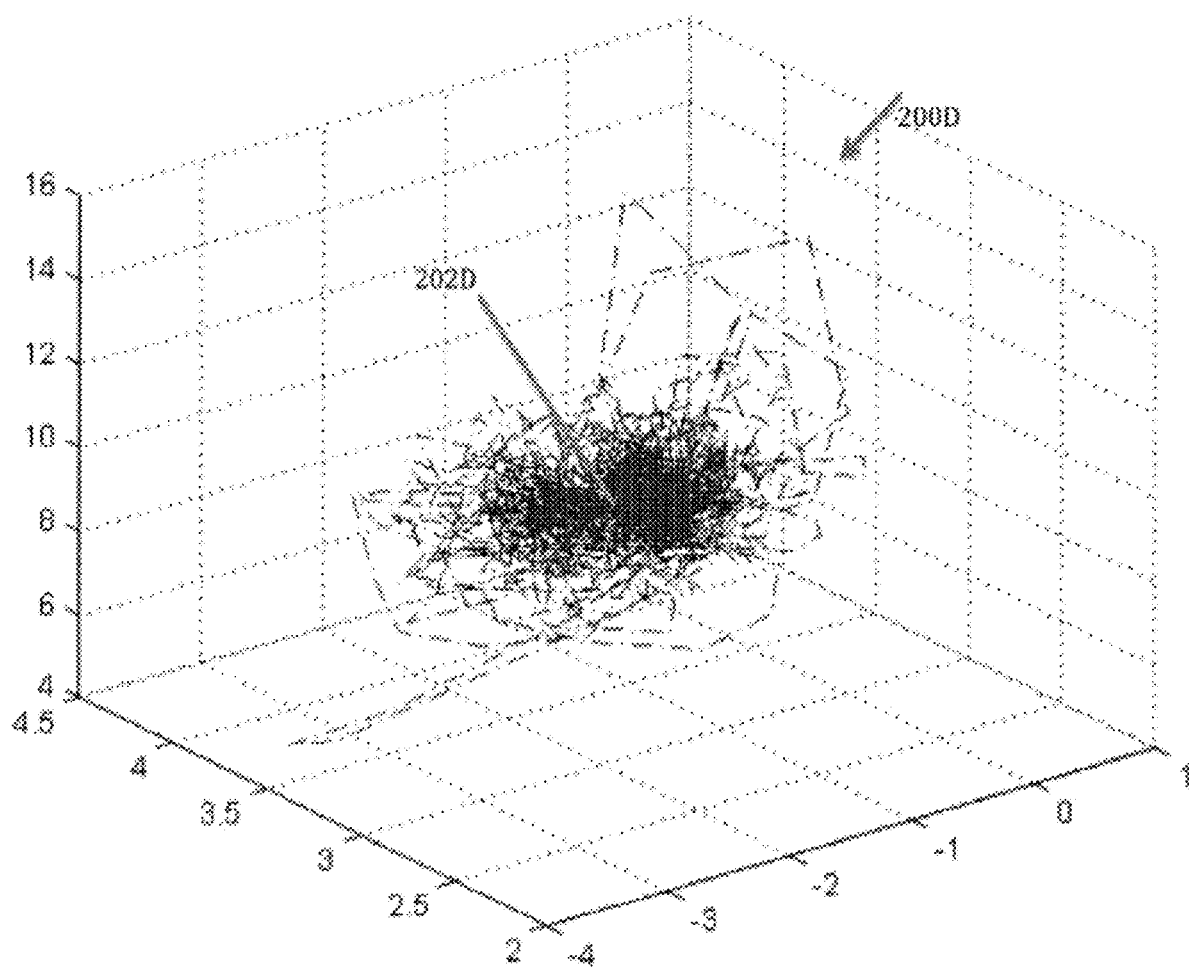

As can be readily seen in FIGS. 2A-2C, the patterns 200A-200D in each of the Poincare' phase plot diagrams generated from the neuro-derived motion of the users are substantially different. For example, a center of mass 202A-202D of each pattern 200A-200D differs. Other characteristics of each pattern 200A-200D also differ for each user. Thus, the pattern of neuro-derived motion is unique to each user and can be used to uniquely identify a user.

The unique patterns 200A-200D in the generated Poincare phase plots and the NFP are normally stable. Thus, normally they can be repeatedly sensed over sample periods of time each time a user touches or moves the sensor and then compared with an initial calibrated NFP using an algorithm to authenticate the identity of a user. However, if there is a neuromuscular disease that is progressing, the unique pattern 200A-200D for a user is less stable. If this is the case, the neurological algorithm can be periodically recalibrated to compensate for disease progression. For example, an elderly person with a neuromuscular disease can easily recalibrate the neurological algorithm on a weekly basis, depending on a drift cutoff relative to an initial calibration for the NFP. As another example, a user who is being treated with motion-altering medications can also recalibrate the NFP neurological algorithm on a periodic basis. For most users, recalibration of the NFP neurological algorithm after an initial calibration will be infrequent.

The analysis of motion signals for micro-motions employs a neurological algorithm to obtain a neuro-mechanical fingerprint (NFP) of a user. Accordingly, this neurological algorithm may be referred to herein as an NFP neurological algorithm.

NFP Neurological Algorithm

A NFP neurological algorithm is not an algorithm that uses neural network training, classifiers, or deep learning. The NFP neurological algorithm is an algorithm that specifically collects, isolates, and analyzes signals from the human nervous system and its interactions with parts of the body connected to the nervous system, such as the muscular system, gland cells, and/or the skin. Activities of interest to analyze signals for micro-motions include the motor control stemming out of our nervous system, the sensorial inputs, and stress responses that are uniquely linked to the anatomy and nervous system of each person.

Consider, for example, a user who moves his or her hand. A kinematic algorithm may record the physical motion over time and analyze it for its velocity, distance, direction, and force, for example. A neurological algorithm collects, isolates, and analyzes the neural activities over time linked to the motion of the hand from an electronic signal, such as a motion signal including micro-motion signals, without performing a brain scan with a brain scanner.

While kinematic motions of body parts can be analyzed for micro-motions using an electronic accelerometer, for example, an electronic touch sensor, such as a touch pad, can be used to analyze the touch of one or more fingers to the touch sensor. The touch sensor can be used to generate a micro-motion signal representing the micro-motions over time at a finger touching the touch sensor. A touch sensor can generate three-dimensional signals representing the X and Y position of a finger against the touch sensor and a Z position representing the pressure applied to the touch sensor. Micro-motions may be included as part of each of the three-dimensional position signals. With a touch sensor, gravity is typically not a factor that needs correction.

By focusing on micro-motion signals and not macro-motion signals, a touch sensor may be used with a neurological algorithm to better emulate a human cognitive interface in a machine. This can improve man-machine interfaces. For example, consider a human cognitive interface between a husband and wife or closely-knit persons. When a husband touches his wife on the arm, the wife can often times recognize that it is her husband touching her just from the feel of that touch, because she is familiar with his touch. If the touch feels unique, a human can often recognize what it is that is touching him/her just from that unique feel.

Touch Recognition

The technique of using of a touch sensor to sense and capture micro-motions and a neurological algorithm to analyze an NFP may be referred to herein as touch recognition. A system that includes touch recognition to authenticate and/or identify a user may be referred to herein as a touch recognition system. With respect to FIG. 1, touch-recognition using NeuroFingerPrints is a physiological user identifier. Touch recognition is not an anatomical user identifier. Touch recognition is not a behavioral user identifier. Contrary to anatomical identification methods, which are fixed attributes of a user, physiological identification methods are linked to the functional body of a user. Behavioral identification methods are linked to what the user does or his/her habits.

Using a touch sensor and a neurological algorithm has intrinsic advantages in user authentication. The user interface for user authentication can be intuitive and linked to the spontaneous behavior of the human user with only minimal training, if any training is needed at all. The user experience of the user authentication process can be frictionless. The user need not perform any specific user authentication task over and above those ordinarily associated with the use of the user's electronic device. For example, after calibration, a user may only need to hold his/her smart phone, such as to make a telephone call, so that an accelerometer and a neurological algorithm perform the user authentication process.

NeuroFingerPrints can be captured non-intrusively by a touch sensor and the NFP neurological algorithm. NeuroFingerPrints can be isolated from other user motions. Accordingly, one or more touch sensors used to capture keystrokes or key depressions may also be used to capture micro-motions of a user and generate micro-motion signals and the NeuroFingerPrints in response thereto. For example, a user may only need select one or more buttons (e.g., dial a telephone number for a telephone call, enter a personal identification number, select a function button or power button) so that one or more touch sensors there-under and a neurological algorithm perform the user authentication process.

Without any change in user experience, a NeuroFingerPrint (NFP) can be generated by the NFP neurological algorithm while a user's personal identification number (PIN) is entered, for example. Alternatively, a NeuroFingerPrint (NFP) can be generated by the NFP neurological algorithm while a power button or a function button (e.g., home button) is pressed for example. In this case, the NeuroFingerPrint (NFP) can be used for user authentication without a PIN number. Alternatively, with little to no user interface change, a NeuroFingerPrint (NFP) can be used conjunctively with a PIN number for user authentication.

With little to no change in a user interface, the one or more touch sensors associated with a keypad or a button can also be used to capture micro-motions and generate micro-motion signals as a user presses or selects the keys of the keypad or the button. The keypad or button that supports NFP capture may be used to control entrances and/or exits to offices, buildings, or other real property, such as homes, businesses, government offices, or other secured facilities.

Moreover, touch sensors combined with the neurological algorithm can advantageously be built into a physical electronic key, which could then be used wirelessly to open a door, start a car engine, or gain access to a server or other information technology system.

Local and Remote User Authentication

Figure 3A:
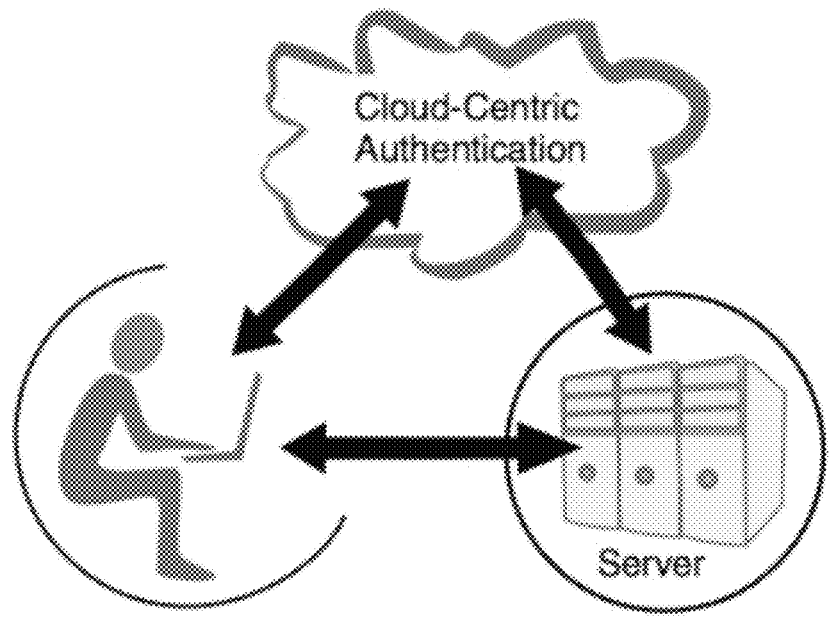
FIG. 3A is diagram illustrating remote authentication of a user over the Internet with a server and a storage device of a storage area network (cloud storage).
Figure 3B:
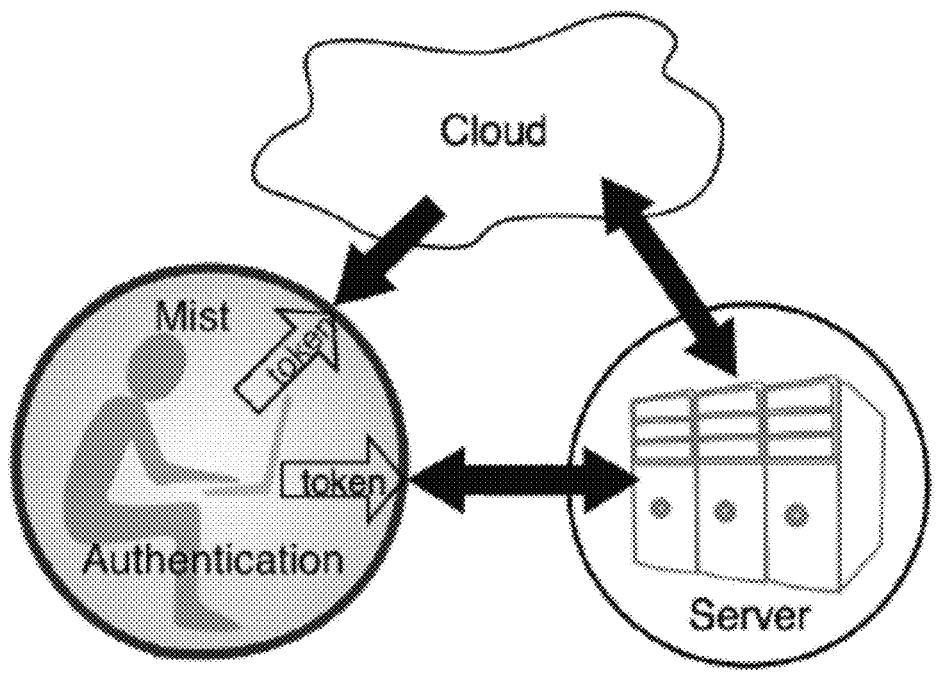
FIG. 3B is diagram illustrating local authentication of a user at a local electronic device.

Reference is now made to FIGS. 3A-3B. FIG. 3A illustrates remote authentication of a user. FIG. 3B illustrates local authentication of a user.

Touch recognition facilitates local authentication of a user at a local electronic device, such as shown in FIG. 3B. NFP user authentication does not require the use of a large remote database. An NFP user authentication system can be self-contained within the local electronic device, such as a mobile smartphone. Data for user authentication needn't be stored in and accessed from a storage device of a storage area network (the "cloud") over the Internet, as may be required for remote authentication. A login ID and password for user authentication need not be sent over the Internet to a server to authentic a user, as may be required for remote authentication. Touch recognition is decentralized and can be self contained within the local electronic device.

With remote authentication of a user, such as shown in FIG. 3A, a user is open to the Internet and may be subject to risks associated with it. With local authentication, such as shown in FIG. 3B, the user may be closed off from the Internet during user authentication to provide added security. A token representing local user authentication may be generated instead by the local electronic device and sent wired and/or wirelessly out from the local electronic device to a local server or remotely over the internet cloud of routers, switches, and communication systems to a remote server such as shown in FIG. 3B.

While touch recognition facilitates local authentication, touch recognition may be readily combined with a remote authentication technique or another local authentication technique to provide additional levels of security.

Multi Factor Authentication and NeuroFingerPrints

Referring now to FIG. 4, a user authentication system may employ multiple factors to authenticate a user. Multi factor authentication combines two or more authentication techniques. Previously, multi-factor authentication was not user-friendly so it was avoided. User-friendly authentication methods were often preferred instead, but led to compromised protection.

As mentioned herein, touch recognition or recognition using an accelerometer may be combined with a remote authentication technique or another local authentication technique so that multi-factor authentication is more user-friendly.

Touch recognition may be combined with a password, a personal identification number, a pattern, or something else a user knows or remembers. Alternatively, touch recognition may be combined with a token, a smart card, a mobile token, an OTP token, or some other user authentication device a user has. Alternatively, touch recognition may be combined with an anatomical or behavioral user biometric. For example, neurological based touch recognition may be readily combined with finger print recognition to provide a user-friendly multi factor authentication system.

The banking industry is particularly interested in avoiding an extra burden on the user when user authentication is required. Moreover, the banking industry is interested in high performance user authentication systems that provide reliable user authentication and are difficult to circumvent. Neurological based touch recognition can be readily combined with other authentication techniques with minimal burden on the user. Moreover, the neurological based touch recognition that is disclosed herein can be substantially reliable and very difficult to circumvent.

Comparison of Biometric Identification Techniques

Referring now to FIG. 5, a chart of a comparison matrix of various biometric identification technologies is illustrated. A relative ranking is used to compare user authentication with NFPs to other biometric user identification techniques. The relative ranking is based on seven rated criteria. Each criterion can be rated high (H), medium (M), or low (L) for each biometric identification technique. From left to right, the seven rated criteria are permanence, collectability, performance, acceptability, circumvention, uniqueness, and universality. The use of NFPs ranked highest over the other biometric identification techniques for the following reasons.

NFP is a highly ranked universal technology. Each and every human being that would be a user has a unique nervous system from which NFPs can be captured.

NFP is highly unique user authentication technology differentiating between users. The NFP reflects a user's motor control of the user's body. Motor control is linked to the brain activity controlling the muscular tone in the hands. Even twins will have different motor control because the will undergo different life's experiences and have different motor skill training. For example, twins will learn to ride a bicycle differently, learning different motor control over muscles that will be reflected in differing NFPs.

NFP is a relatively highly permanent or stable technology because it is linked to each person's anatomy. Evolutive processes, such as a neurological disease that can affect the stability of NFPs, are rare. Even in those rare cases, the neurological evolution process is usually sufficiently slow such that an NFP user authentication system can be recalibrated. The NFPs for touch recognition differs for a user's left hand and a user's right hand. However, they are each user specific NFPs. A user can be consistent in what hand/finger that he/she uses to hold/touch an accelerometer enabled device/touch sensor enabled device. Alternatively, multiple NFPs for the same user can be calibrated with the NFP user authentication system. In this case, the touch of either hand or multiple fingers may authenticate a user of an electronic device.

Some neurotropic medications can alter the scanned NFP. However, the NFP user authentication system can be re-calibrated to compensate. In other cases, the alteration of the scanned NFP due to the intake of alcohol, drugs, or strong medications, can be used to improve safety of vehicles.

Alcohol can temporarily alter a scanned NFP so that it does not match a calibrated NFP. This could be advantageously used to prohibit driving a car or other vehicle under the influence of alcohol. For example, the NFP touch technology could be implemented within a car key or a car's start button. If the scanned NFP is unaffected by alcohol, the NFP touch technology allows key or start button to start up the engine to drive the car. If the scanned NFP is affected by a user drinking alcohol, the NFP touch technology can prohibit the key or start button from starting the engine of the car.

NFPs are relative easy to collect or capture because accelerometers have become common in mobile devices. Accelerometer values are frequently sampled with a clock at or around a microsecond to capture micro-motions of a user. Moreover, accelerometers are relatively sensitive. Accelerometers often can sense submicro-levels of accelerations such that they are capable of capturing micro-motions of a user's hand for example. Various three dimensional accelerometers may be used to capture micro-motions of a user's hand. Various touch sensors may be used to capture micro-motions and the type, whether capacitive or resistive, is not relevant.

The performance of NFP authentication with NFPs is high. Using non-optimal math algorithms as the neurological algorithms can achieve recognition success rates between 93 percent and 97 percent. More appropriate and accurate mathematic algorithms that consider variables of time and trajectory can achieve higher recognition success rates to reach 100 percent recognition of a proper user. An alternate user authentication system, such as a PIN, may be used in parallel with NFP authentication in case the NFP authentication system fails to recognize a proper user. In comparison, most biometrics (except for real fingerprints or iris scan) have low performance with higher failure rates that can range between 18-20% providing between 80 and 82 successful recognition rates.

NFP technology should have a high level of acceptability because it is a user-friendly authentication method. An NFP user authentication system can be fairly transparent or friction-less. However, acceptability is also subject to how the NFP user authentication system is designed and marketed, along with how it is supported by appropriate safety measures and independent auditing.

NFPs are difficult to circumvent so they have a high rating for the circumvention factor. Hacking, spoofing or reverse-engineering to gain access can be made nearly impossible when the NFP authentication system resides in the electronic device and is unavailable to the Internet.

A calibration NFP file (user calibration parameters) is initially generated electronically for a user locally by the NFP user authentication system. The calibration NFP file is typically encrypted and saved locally on the electronic device (e.g., in memory associated with the NFP authentication controller) and is thereof unavailable to the Internet. However, when stored elsewhere, such as a storage device in a storage area network or a storage device associated with an authentication server, the calibration NFP file should be encrypted to provide greater security.

NFP user authentication does not simply perform a file comparison to grant access. The NFP has to be regenerated from the user's body in real time to gain access. This avoids a hacker from using a stolen file to gain access and authorization to the electronic device by using a surrogate misleading input, or a spoofing or a phishing event for information. To circumvent NFP user authentication at the service level, the hacker would have to concurrently make the data acquisition in parallel to the authorized user, while the user is accessing a service that requires authentication or login. To circumvent NFP user authentication at the device level, a hacker would have to emulate the neurological control of the authorized user to obtain the NFP data and then enter into it into the device to gain access. A hacker could steal the calibrated NFP value from the authorized user's device, but then the hacker would have to impossibly regenerate the user's micro-motion input into a second electronic device with the same calibrated NFP authentication system. Accordingly, an electronic device with an NFP authentication system can be extremely difficult to circumvent. A mobile electronic device with an NFP authentication system can ultimately be trusted as a user's gatekeeper providing real-time validated identification.

Only when a user utilizes the electronic devices is a scanned NFP subsequently generated in real time, with the calibrated NFP only adjusting the calculations. Without the proper user that generated the calibrated NFP file, the NFP authentication system denies local access to the electronic device. If the proper user is not alive, the NFP authentication system will deny access because the micro-motion signals of the proper user cannot be generated. Accordingly, circumvention of the NFP authentication technology is difficult. By comparison, classical fingerprints have a high difficulty level of circumvention, however, even classical fingerprints can be stolen and reverse-engineered to login into a fingerprint authentication system.

Overall, NFP technology as the biometric for a user authentication system is ranked highly when compared to other biometric technologies.

Privacy Protection

Mobile electronic devices are being used with health and fitness applications. In some cases, they may be used as the user interface to connected medical devices. Rules and laws in a number of countries regulate privacy of a user's medical condition. Accordingly, protection of a user's medical condition and medical data has become increasingly important.

An NFP authentication system can be used to help protect a user's data that may be stored or input into an electronic device. An NFP authentication system can be used to help comply with the laws and regulations of medical data that are in effect in a number of countries.

The NFP data that is generated from micro-motions as a result of a user's neurosystem may be considered a form of medical data. The NFP authentication system can be implemented to effectively protect the calibrated NFP data that is stored in an electronic device or elsewhere when used for the purpose of authentication.

Micro-Motions and Tremors

The NFP is generated in response to micro-motions that are related to a type or form of tremor. A tremor is an unintentional, rhythmic muscle movement that causes an oscillation in one or more parts of a human body. Tremors may be visible or invisible to the unaided eye. Visible tremors are more common in middle aged and older persons. Visible tremors are sometimes considered to be a disorder in a part of the brain that controls one or more muscles throughout the body, or in particular areas, such as the hands and/or fingers.

Most tremors occur in the hands. Thus, a tremor with micro-motions can be sensed when holding a device with an accelerometer or through a finger touching a touch pad sensor.

There are different types of tremors. The most common form or type of tremor occurs in healthy individuals. Much of the time, a healthy individual does not notice this type of tremor because the motion is so small and may occur when performing other motions. The micro-motions of interest that are related to a type of tremor are so small that they are not visible to the unaided eye.

A tremor may be activated under various conditions (resting, postural, kinetic) and can be often classified as a resting tremor, an action tremor, a postural tremor, or a kinetic or intention tremor. A resting tremor is one that occurs when the affected body part is not active but is supported against gravity. An action tremor is one that is due to voluntary muscle activation, and includes numerous tremor types including a postural tremor, a kinetic or intention tremor, and a task-specific tremor. A postural tremor is linked to support the body part against gravity (like extending an arm away from the body). A kinetic or intention tremor is linked to both goal-directed and non goal-directed movements. An example of a kinetic tremor is the motion of a moving a finger to one's nose, often used for detecting a driver for driving under the influence of alcohol. Another example of a kinetic tremor is the motion of lifting a glass of water from a table. A task-specific tremor occurs during very specific motions such as when writing on paper with a pen or pencil.

Tremors, whether visible or not to the eyes, are thought to originate in some pool of oscillating neurons within the nervous system, some brain structures, some sensory reflex mechanisms, and/or some neuro-mechanical couplings and resonances.

While numerous tremors have been described as either physiologic (without any disease) or pathological, it is accepted that the amplitudes of tremors is not very useful in their classification. However, the frequencies of tremors are of interest. The frequencies of tremors allow them to be used in a useful manner to extract a signal of interest and generate a unique NFP for each user.

FIG. 6 illustrates a table of various tremor types, their activation condition, and the expected frequency of motion due to the given tremor type.

Numerous pathological conditions like Parkinson (3-7 Hz), cerebellar diseases (3-5 Hz), dystonias (4-7 Hz), various neuropathies (4-7 Hz) contribute motions/signals to the lower frequencies, such as frequencies at 7 Hertz (Hz) and below. Because pathological conditions are not common to all users, these frequencies of motions/signals are not useful for generating NFPs and are desirable to filter out. However, some of the embodiments disclosed herein are used to specifically focus on those pathological signals as a way to record, monitor, follow said pathologies to determine health wellness or degradation.

Other tremors, such as physiological, essential, orthostatic, and enhanced physiological tremors can occur under normal health conditions. These tremors are not pathologies per se. Accordingly, they are often present in the population as a whole. Physiological tremors, as well as others that are common to all users, are of interest because they generate micro-motions at frequencies over a range between 3 to 30 Hz, or 4 to 30 Hz. They may be activated when muscles are used to support body parts against the force of gravity. Accordingly, holding an electronic device in one's hand to support the hand and arm against gravity can generate physiological tremors that can be sensed by an accelerometer. Touching a touch pad of an electronic device with the finger of a hand and supporting it against gravity, can generate physiological tremors that can be readily sensed by a finger touch pad sensor.

Some tremors may be the result of a degenerative pathology or other common pathology that affects the health of a user. Given that nerve cells are highly sensitive to metabolism, other pathologies like diabetes, hypertensive disease, cardiac failure, bacterial or viral infections, and/or parasitic diseases may affect the micro-motions in a user in a common data pattern or signature in a neuro-mechanical fingerprint or micro-motions signal.

Essential tremors of a kinetic type, may occur and be sensed when a user has to enter a PIN or login ID to gain access to a device or a phone. The frequency range of essential tremors is between 4 to 12 Hz that could be reduced to a frequency range of 8 to 12 Hz to avoid sensing for tremors that are due to uncommon pathological conditions.

For the physiological tremor (or the enhanced physiological tremor, idem with larger amplitudes), the coherence of different body sides is low. That is a physiological tremor on the left body side is not very coherent to a physiological tremor on the right body side. Accordingly, it is expected that tremors in the left hand or finger will differ from tremors in the right hand or right finger of a user. Accordingly, the NFP authentication system will require a user to be consistent in using the same side hand or finger for authentication; or alternatively, multiple authorized user calibration parameter sets, one for each hand or one for each finger that will be used to extract an NFP.

Motions with a higher frequency of interest may be considered to be noise. Accordingly, signals with a frequency higher than the maximum in desired range (e.g., 12 Hz or 30 Hz) in the raw motion signal are desirous to be filtered out. Thus, a frequency signal range from 8 Hz to 12 Hz, and/or 8 Hz to 30 Hz contains useful information regarding micro-motions that can be used to generate NFPs.

The raw signal, captured by a finger touch pad sensor in an electronic device or by an accelerometer of a hand held electronic device, can have a number of unwanted signal frequencies in it. Accordingly, a type of filtration having a response to filter out signals outside the desired frequency range can be used to obtain a micro-motions signal from the raw electronic signal. Alternatively, an isolation/extraction means for signals in the desired frequency range may be used to obtain a micro-motions signal from the raw electronic signal. For example, a finite impulse response bandpass filter (e.g., pass band of 8 to 30 HZ) can be used to select the low signal frequency range of interest in a raw electronic signal sensed by a touch pad or accelerometer. Alternatively, a low-pass filter (e.g., 30 Hz cutoff) and a high-pass filter (e.g., 8 Hz cutoff) or a high-pass filter (e.g., 8 Hz cutoff) and a low-pass filter (e.g., 30 Hz cutoff) can be combined in series to achieve a similar result.

Electronic Device with NFP Authentication

Figure 7:
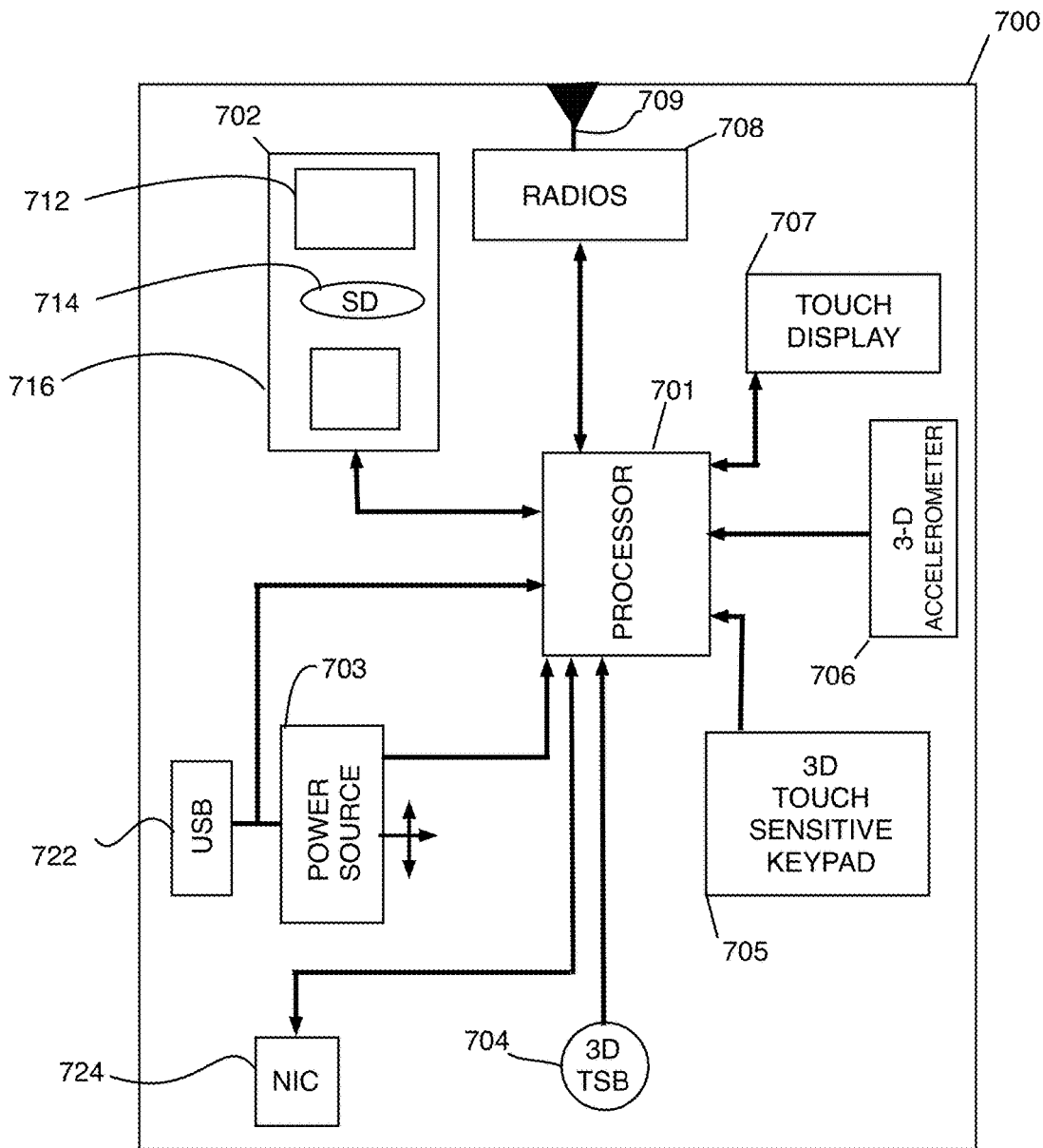
FIG. 7 is a functional block diagram of an example of an electronic device including sensors to capture micro-motion signals from a user and an NFP authentication system to control access in response to the micro-motion signals.

Referring now to FIG. 7, a functional block diagram of an electronic device 700 with NFP authentication is illustrated. The electronic device 700 may be a smart cellular telephone, for example, or other hand held type of portable or mobile electronic device for which access control is desirable. The electronic device 700 includes one or more three-dimensional (3-D) sensors that may be used to capture raw 3-D electronic signals that include raw 3-D micro-motion signals that can be used for NFP authentication.

The electronic device 700 may include a processor 701, a storage device (SD) 702, a power source 703 (e.g., rechargeable batteries), a button/pad 704, a keypad 705, a three-dimensional (3-D) accelerometer 706 (optionally), a display device 707, one or more wireless radios 708, and one or more antennae 709 coupled together. If the electronic device does not have a three-dimensional (3-D) accelerometer 706, one or more of the button/pad 704, the keypad 705, and the display device 707 are touch sensitive so they may be used to capture 3-D raw electronic signals that include the 3-D micro-motion signals.

The storage device 702 is preferably a non-volatile type of storage device that stores data, instructions, and perhaps other information (e.g., user calibration parameters) in a non-volatile manner so it is not lost when the electronic device goes to sleep to conserve power or is fully powered off. The storage device 702 stores software applications instructions 712, NFP instructions and possibly NFP data 714 (e.g., calibration NFP file of authorized user calibration parameters) for the NFP authentication system, and user scratch pad data 716 for the user. The NFP instructions and NFP data 714 is separate from the user scratch pad data 716 and the software application instructions 712 for security reasons to make it is inaccessible to all users. The storage device 702 is coupled to the processor 701 so that data and instructions can be read by the processor and executed to perform functions of software applications. The NFP instructions and NFP data 714, if any, is read by the processor to execute the NFP authentication controller module and perform the functions needed to provide NFP authentication.

The one or more radios 708 are coupled to and between the processor 701 and the one or more antennae 709. The one or more radios 708 can wirelessly receive and transmit date over wireless networks. The one or more radios 708 may include a Wi-Fi radio for local wireless (Wi-Fi) networks, a cellular radio for cellular telephone networks, and blue tooth radio for Bluetooth wireless connections. Software applications may be executed by the electronic device that require authentication to a remote server. The NFP authentication system is used to grant access to the electronic device itself. However, the NFP authentication system may also be used by software applications to verify or authenticate the identity of an authorized user.

To recharge batteries or provide an alternate power source, a power connector and or a combined power/communication connector (e.g., universal serial bus connector) 722 may be included as part of the electronic device 700. The connector 722 may couple to the processor 701 for data communication and to the power source 703 to recharge batteries and/or provide an alternate power source for the electronic device 700. For wired connectively, the electronic device 700 may further include network interface controller and connector 724, such as an Ethernet controller and port connector (e.g., RJ-45), coupled to the processor.

More portable or mobile electronic devices now include 3-D accelerometers 706. The 3-D accelerometers 706 have traditionally been used to determine orientation of the electronic device. However, the 3-D accelerometer 706 can also be used to capture the micro-motions of a user's hand that holds the electronic device 700. In this case, the 3-D accelerometer data is captured by the accelerometer 706, sampled, pre-processed, and then provided to the NFP authentication controller.

If the accelerometer is unavailable in an electronic device, either one or both of the button/pad 704 and keypad 705 are touch sensitive in three dimensions including X, Y, and Z to use for NFP authentication. The Z axis is the axis perpendicular to the button and keypad along with pressure may be exerted by a finger to select the underlying function of the button or key of the keypad to control the electronic device. The button/pad 704 may be a power button for example to power the electronic device on/off, for example. The button/pad 704 may be a home button for example, that brings the electronic device to a "home" or initial user interface state.

Either or both of a touch sensitive button/pad 704 and/or a touch sensitive keypad 705 may be used to capture three dimensions of raw micro-motion signals that can be used for NFP authentication.

If the display device 707 is a touch sensitive display device, the keypad 705 or button 704 may be displayed on the touch sensitive display device 707 from which the three dimensions of raw micro-motion signals may be captured.

Portions of an NFP authentication controller (see NFP authentication controller 810A-810C, 810 in FIGS. 8A-8C, 14A) may be formed by the processor 701 executing instructions recalled from the firmware/software 712 stored in the storage device 702.

Figure 8A:
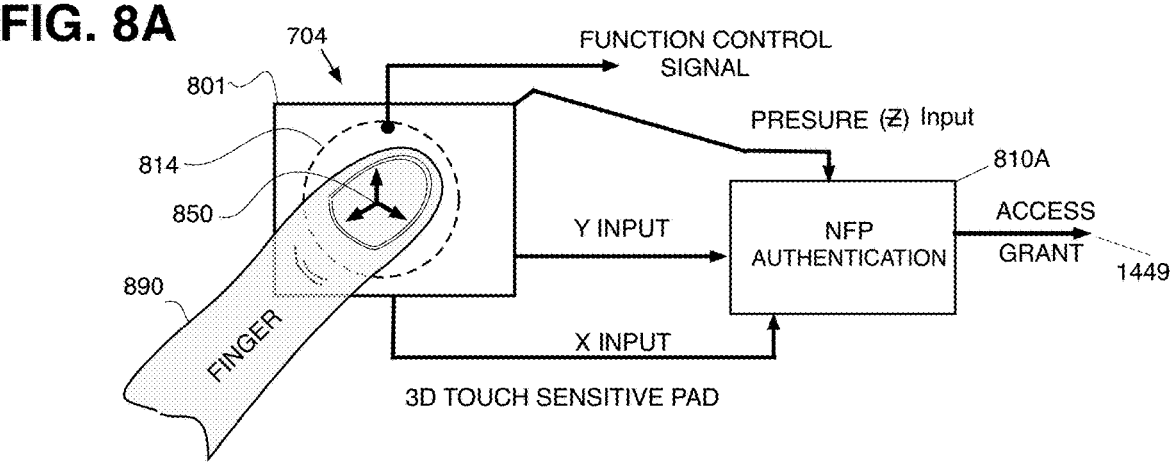
FIG. 8A-8C are NFP authentication systems with differing sensors to sense micro-motions from a finger or from a hand.

Referring now to FIGS. 7 and 8A, a functional block diagram of a portion of an NFP authentication system with a three-dimensional touch sensitive button/pad 704 is shown. The NFP authentication system further includes an NFP authentication controller 810A coupled to the touch sensor 801 of the three-dimensional touch sensitive button/pad 704.

The three-dimensional touch sensitive button/pad 704 includes a 3D touch sensor 801 nearest the surface of the pad 704 to sense the position and changes in the X, Y finger position and finger pressure Z. The three-dimensional touch sensitive button/pad 704 typically includes a functional button switch 814 that is used to generate a function control signal that is sent to the processor. The 3D touch sensor 801 generates the raw three-dimensional displacement signals that includes the micro-motions indicated by the 3D arrow 850 that are sensed at the user's finger 890.

After some preprocessing, the NFP authentication controller 810A receives the data samples representing the micro-motions sensed by the touch sensor 801 and generates the NFP for the user. A calibration NFP file of authorized user calibration parameters is typically stored in a non-volatile memory or other non-volatile storage device within the NFP authentication controller or a non-volatile memory or other non-volatile storage device coupled to or coupled in communication with (e.g., memory 702, or a storage device of a server) the NFP authentication controller. In response to the NFP and stored user calibration parameters that were trained by and associated with the authorized user, the NFP authentication controller 810A classifies the NFP and generates a match percentage value. In response to the match percentage value and a predetermined acceptable match percentage, the NFP authentication controller 810A can generate an access grant signal 1449 that grants access to the electronic device for the authorized user that is touching the touch sensor. The NFP authentication controller 810A may be a functional process that a processor (e.g., the processor 701) is configured (by hardware, software, or a combination of hardware and software) to perform.

Figure 8B:
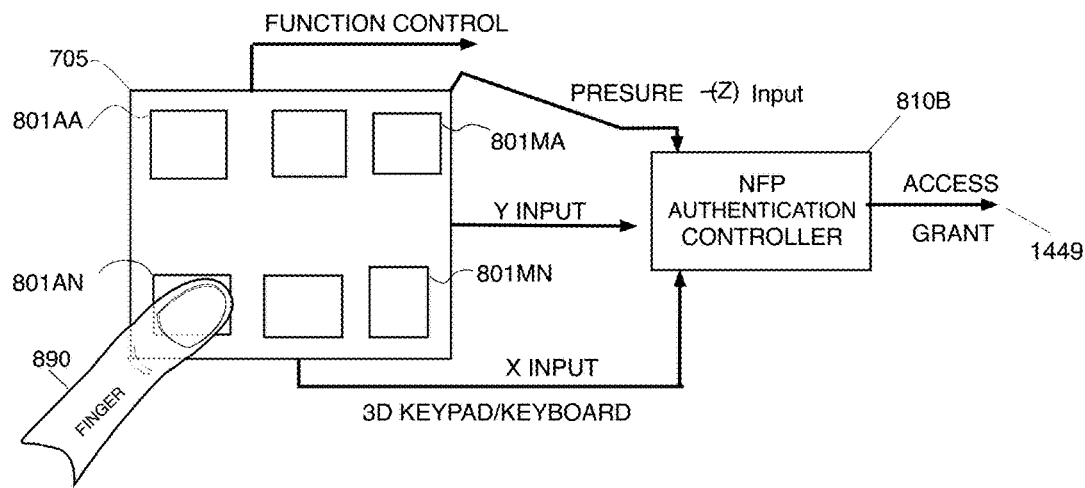

Referring now to FIGS. 7 and 8B, a functional block diagram of an NFP authentication system with a three-dimensional touch sensitive keypad 705 is shown. The touch sensitive keypad 705 includes a matrix of an M by N array of 3D touch sensors 801AA-801MN each of which can sense the position and changes in the X, Y finger position and finger pressure Z of a finger 890 and generate the raw micro-motions data. Each pad may include a functional button switch 814 to concurrently generate a plurality of functional control signals while the raw micro-motions sensor data is being captured by the 3D touch sensors 801AA-801MN.

The signals from M by N array of 3D touch sensors 801AA-801MN is preprocessed and sampled with the sampled data being coupled to the NFP authentication controller 810B. The NFP authentication controller 810B acts similar to the NFP authentication controller 810A in granting access. However, the training of the NFP authentication controller 810B may be made to support slightly different signals that can be expected from the different touch sensors in the matrix of the M by N array of 3D touch sensors 801AA-801MN.

Accordingly, the calibration NFP file of authorized user calibration parameters may differ for each different touch sensor. It is expected the calibration NFP file of authorized user calibration parameters may be larger with user calibrations parameters for each of the plurality of touch sensors. With a larger calibration NFP file, the non-volatile memory or other non-volatile storage device that stores the file may be somewhat larger having a slightly larger capacity. Similarly, a non-volatile memory or other non-volatile storage device coupled to or coupled in communication with (e.g., memory 702, or a storage device of a server) the NFP authentication controller may have a larger storage area and/or capacity to accommodate a somewhat larger NFP calibration file from one or more users. The NFP authentication controller 810B may be a functional process that a processor (e.g., the processor 701) is configured (by hardware, software, or a combination of hardware and software) to perform.

Figure 8C:
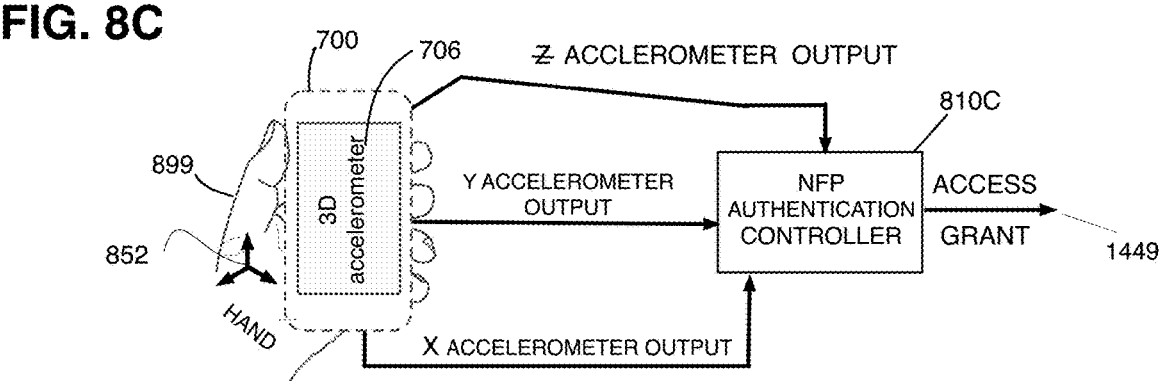

Referring now to FIGS. 7 and 8C, a functional block diagram of an NFP authentication system with a three-dimensional accelerometer 706 in an electronic device 700 is shown. A users hand 899 holds the electronic device 700 that includes the three-dimensional accelerometer 706. The three-dimensional accelerometer 706 is coupled to the NFP authentication controller 810C. The NFP authentication controller 810C may be a functional process that a processor (e.g., the processor 701) is configured (by hardware, software, or a combination of hardware and software) to perform.

While holding the electronic device 700 steady in his/her hand 399, the micro-motions indicated by the 3D arrow 852 in the user's hand 899 are sensed by the 3D accelerometer 706. As the electronic device 700 held in the users hand is moved about to adjust positions, such as from a pocket to the user's ear, undesirable macro-motions are also sensed by the 3D accelerometer 706 in addition to the micro-motions. As further explained herein, these undesirable macro-motions are to be suppressed, filtered out, or eliminated in the desired signal.

Touch sensors typically differ from a 3D accelerometer. Accordingly, the NFP calibration file of authorized user calibration parameters will likely differ. Some calibration data, generated as filter parameters of a digital filter to filter out unwanted motions (e.g., micro-motions) in the three-dimensional accelerometer signals from the 3D accelerometer, may be included as part of the NFP calibration file associated with the user. Accordingly, the NFP calibration file of authorized user calibration parameters for a 3D accelerometer can differ from the NFP calibration file of authorized user calibration parameters for a touch sensor. In either case, the NFP calibration file of authorized user calibration parameters is typically stored in a non-volatile memory or other non-volatile storage device within the NFP authentication controller or a non-volatile memory or other non-volatile storage device coupled to or coupled in communication with (e.g., memory 702, or a storage device of a server) the NFP authentication controller.

The raw three-dimensional accelerometer signals generated by the 3D accelerometer 706 are preprocessed and undergo compensation due to the force of gravity. The raw three-dimensional accelerometer signals are sampled into data samples of a dataset so that digital signal processing can be used to digitally filter and perform digital transformations with a digital processor, such as processor 701 shown in FIG. 7. The data samples of the accelerometry data are coupled into the NFP authentication controller 810C.

The NFP authentication controller 810C receives the data samples representing the micro-motions sensed by the accelerometer 706 and generates the NFP for the user. In response to the NFP and stored user calibration parameters that were trained by and associated with the authorized user, the NFP authentication controller 810C classifies the NFP and generates a match percentage value. In response to the match percentage value and a predetermined acceptable match percentage, the NFP authentication controller 810C can generate an access grant signal 1449 that grants access to the electronic device for the authorized user that is holding the electronic device.

While three dimensional sensors (e.g., 3D touch sensor, 3D accelerometer or 3D motion sensor) have been described herein to capture a three dimensional micro-motions signal as a three dimensional signal to generate an NFP, the sensors may be multi-dimensional to capture a multi-dimensional signal with at least two dimensions. For example, a touch sensitive surface may capture a varying impedance having two varying dimensions of resistance and capacitance that could be used to generate a three dimensional representation of an NFP from a varying two dimensional signal.

Signal Processing

Figure 14A:
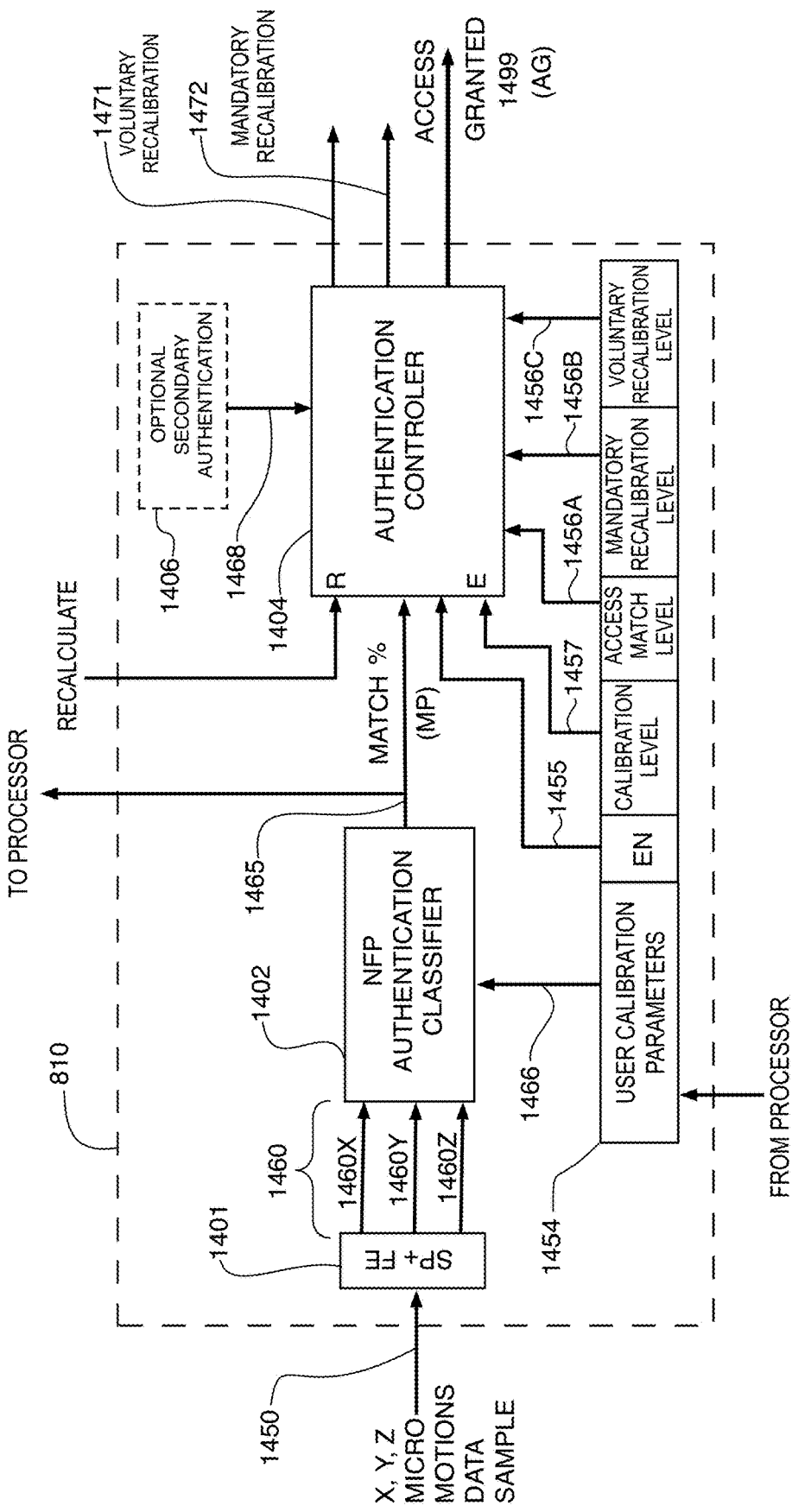
FIG. 14A is a functional block diagram of an NFP authentication controller.

Referring now momentarily to FIG. 14A, to obtain an NFP 1460 from the sampled micro motion signals 1450 captured by a sensor and sampled by a sampler (A-to-D converter), a number of signal processing steps are performed by the processor in the electronic device. The signal processing steps performed on each dimension of the sampled micro motion signals 1450 are performed by the signal processing and feature extraction module 1401 of the NFP authentication system 810. These one or more signal processing algorithms performed by the module 1401 may be generally be referred to herein as the NFP algorithm and method.

Generally, a sequence of events are performed to obtain an NFP for a user and then evaluate its authenticity.

Raw data files (in the X, Y and Z direction) over a predetermined sample period are obtained from 3D accelerometers, or one or more touch pad sensors as the case may be.

The raw data files are sampled over predetermined time spans (e.g., 5, 10, 20 or 30 seconds) with a predetermined sampling frequency to capture signals of interest that is compatible with the further filtering needed (e.g., 250 Hz (4 msec between samples), 330 Hz, 200 Hz, or down to 60 Hz, twice the 30 Hz frequency of interest).

Signal processing is performed on the sampled signals to generate a micro-motions signal with specific frequency components of interest. The sampled signals are filtered using a band pass filter the frequency range between 7-8 Hz, 7-12 Hz, or 8-30 Hz. This frequency range of micro-motions signals is most useful in distinguishing users from one another. The band pass filter can also suppress large amplitude signals due to voluntary or un-voluntary movements that may be captured by a sensor, such as an accelerometer. If an accelerometer is used as the sensor, the influence of the gravitational force is compensated or removed by signal processing. If an accelerometer is used as the sensor, the sampled signals are made position invariant or orientation invariant by signal processing. The micro-motions signal is a position invariant sampled signal that can be consistently used to extract values of features for comparison between users.

Additional signal processing is performed on the micro-motions signal to generate a signal processed waveform signal from which values for an NFP can be extracted. Predetermined features are selected for which values are to extracted to represent the NFP. The values for an NFP may be extracted directly from the signal processed waveform signal, from each micro-motions signal, and/or from both after additional signal processing is performed. Regardless, unique values are extracted representing a unique NFP for a user that will differ from other NFPs generated by other users.

The user's NFP may be used in a number of different applications. Match result values (e.g., percentages) are generated using a classifier (various data mining techniques can be used as the classifier). The classifier is trained/calibrated with an initial NFP (a calibration NFP) generating authorized user calibration parameters so that a calibration match result level is achieved. Thereafter, the classifier may be used in a user mode with the authorized user calibration parameters. The classifier in the user mode generates match results values to authenticate a user as an authorized user or not. An authentication controller, in response to a predetermined access match level, can determine if a user is an authorized user or not based on the match results value.

A number of these signal processing steps are further elaborated herein.

Signal Sampling

Figure 9:
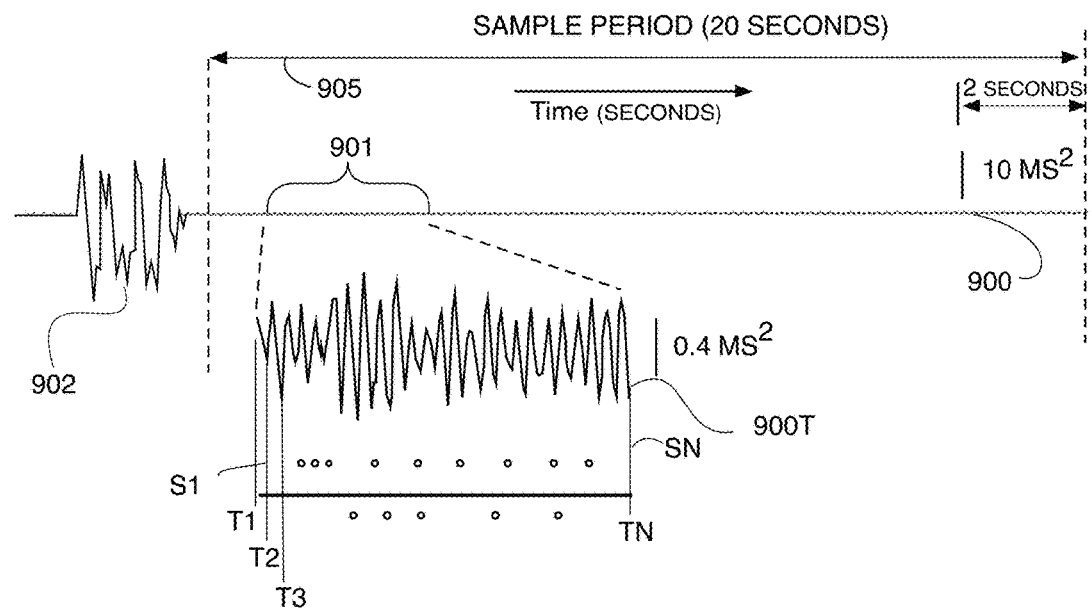
FIG. 9 is a waveform diagram of acceleration measured at a user's hand to show the difference between macro-motions and micro-motions.

Referring now to FIG. 9, a hand acceleration waveform 900 of a hand acceleration signal for a single axis (X, Y, or Z) is shown over time. A portion 901 of the hand acceleration waveform 900 is magnified as waveform 900T as shown. While analog signal waveforms may be shown in the drawings, it is understood that analog signal waveforms may be sampled over time and represented by a sequence of digital numbers at discrete periodic time stamps (a "digital waveform"). While an accelerometer senses acceleration over time, if a sensor senses displacement over time instead, it may be converted into acceleration by twice differentiating the displacement signal with time.

The hand acceleration for each axis is sampled over a predetermined sample time period 905, such as 10, 20 or 30 seconds time spans for example. The sampling frequency is selected so that it is compatible with the filtering that follows. For example, the sampling frequency may be at 250 Hz (4 milliseconds between samples). Alternatively, the sampling frequency can be 330 Hz or 200 Hz, for example. The sampling may be performed on an analog signal by a sampling analog to digital converter to generate the samples S1-SN represented by a digital number over the time stamps T1-TN during the given predetermined sample time period. Assuming a 20 second sample time period and a sampling frequency of 250 Hz, a dataset for acceleration would include 3 (3 axis) times 5000 samples over the time period for a total of 15 k samples.

Signal Normalization for Un-Correlated Signals

Figure 10A:
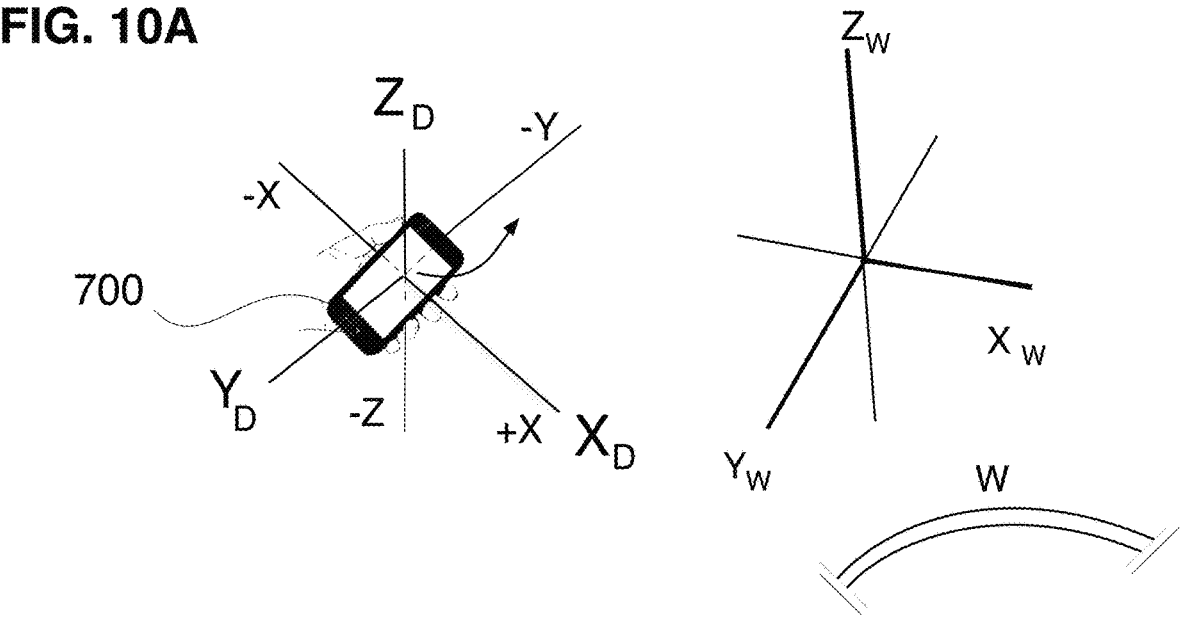
FIG. 10A is a diagram illustrating device orientation and world orientation.

The generation of the NFP is based on un-correlated signals in three dimensions. The 3D accelerometer to sense tremors is part of the electronic device that is held by a user's hand. As shown in FIG. 10A, the device 700 and the device axes Xd, Yd, Zd can be held by the user's hand at different orientations with respect to the world W and world axes Xw, Yw, Zw. Accordingly, the raw sensor data from the 3D accelerometer for the device axes Xd, Yd, Zd is correlated. Thus, the raw sensor data from the 3D accelerometer for the device axes Xd, Yd, Zd is dependent on the orientation of the electronic device 700. A signal normalization process is performed using principal component analysis (PCA) to make the 3D accelerometer data for each axis orientation-invariant or rotation-invariant and thus un-correlated.

Each dataset of raw sensor data from the 3D accelerometer for the device axes Xd, Yd, Zd over a given sample time period is analyzed in the 3D-feature space. Three eigenvectors and eigenvalues are determined for each axis. The eigenvalues of each eigenvector are compared to determine the largest eigenvalue that identifies the largest eigenvector. The points of the data sets are then rotated (points and their data values are transformed in space) so that the largest eigenvector aligns with and along a predetermined axis. The predetermined axis is a constant for all datasets of 3D raw sensor data originating from the same electronic device 700. The predetermined axis may even be a constant for any device that implements the NSP algorithm with a 3D accelerometer. The predetermined axis may be the Zw world axis for example. Aligning the largest eigenvector of each dataset along the predetermined axis transforms the X,Y,Z components of 3D points in the raw sensor data so that they are uncorrelated and rotation-invariant.

Figure 10B:
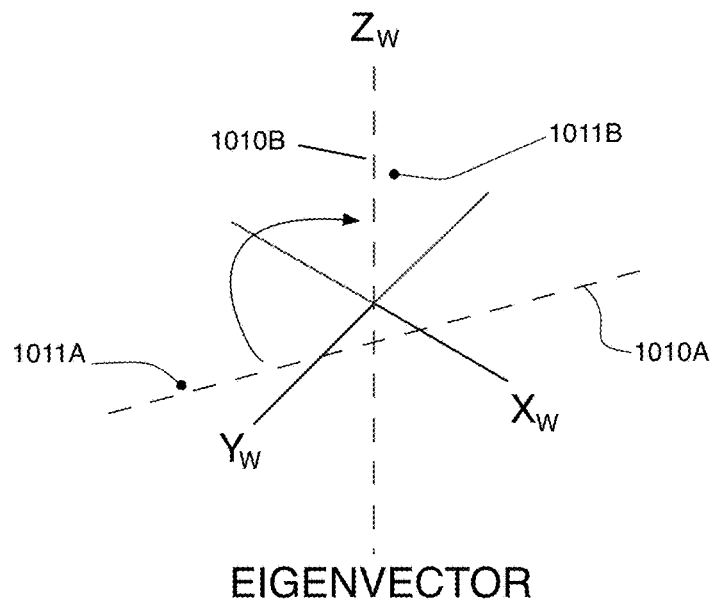
FIG. 10B is a diagram illustrating use of an eigenvector to transform 3-D data samples in a dataset from device orientation to world orientation.

For example, FIG. 10B illustrates a 3D point 1011A of acceleration with respect to an eigenvector 1010A. The data set that forms the eigenvector 1010, including the point 1011A is rotated in 3D space to eigenvector 1010B that aligns with the Zw world axis. The point 1011A and its X,Y,Z component values are transformed in 3D space to point 1011B and its X',Y',Z' component values as a result.

Signal Suppression/Extraction/Filtering

This NFP algorithm specifically extracts tremors or micro-motions from the transformed sensor data signals that are linked with the motor control of the brain cortex, its subcortical parts, cerebellum, central nervous system influenced or not by peripheral structures (e.g., muscular, skeletal, glandular, etc.) and suppresses unwanted parts of the transformed sensor data signals.

Accordingly, it is desirable to generate or extract a micro-motions signal from the transformed hand acceleration signal. However, the transformed hand acceleration signal may have a number of undesirable signals within it that can suppressed, removed, or filtered out. For example, a hand holding the electronic device is often moved around with large movements, such as by moving from ones pocket/purse or pocket so that a keypad is accessible and a display screen is visible.

Large swings 902 in acceleration can occur due to such large movements as is shown in FIG. 9. In some cases, these large swings in a signal from a user's large motions (macro-motions) are useful as a behavior profile, such as described in U.S. patent application Ser. No. 13/823,107 filed by Geoff Klein on Jan. 5, 2012, entitled METHOD AND SYSTEM FOR UNOBTRUSIVE MOBILE DEVICE USER RECOGNITION. However, because these large swings have little to do with micro-motions associated with a neuromuscular tremor, in this case it is desirable to suppress or remove these large swings during signal processing and the generation of a unique NFP for a user.

Unwanted signal components such as attributed to large swings 902 can be suppressed. The large swings may be from vibrations linked to buildings or structures where a user is located, or from the motions that the user actually executes while holding the electronic device with the accelerometer sensor.

Most buildings and structures resonate at a frequency between 3 Hz and 6 Hz. Accordingly, the vibrations from buildings and structures are outside the desirable range of frequencies (e.g., outside the range of 8 Hz to 30 Hz) and are unlikely to resonate and contaminate the desirable signals with the range. Signals in the range of 3 Hz and 6 Hz are to be subsequently filtered out.

The large scale motions (macro-motions) of a user include jumping around with the electronic device, moving one's arm with the electronic device, turning around with the electronic device, walking running, jogging, and other large body movements with the electronic device. The large scale motions (macro-motions) of a user are generally not useful in the generation of NFPs. The NFP algorithm is not based on hands or body attitudes, nor is the NFP algorithm based on motions repertoires/libraries.

The large scale motions (macro-motions) of a user form large scale signal swings 902 shown in FIG. 9 for example. The large scale motions of a user are not likely to be repeated when trying to regenerate an NFP during the authentication process. Large scale motions of a user may unfavorably skew an algorithm or calculation in the generation of an NFP. Accordingly, large scale signals from large scale motions are partially suppressed or filtered out from the acquired data by the band pass filtering that is performed for the desired range of frequencies. The large scale signals from the large scale motions are highly correlated over relatively long time periods. The three dimensions of micro-motions due to the neurological system are not well correlated. Accordingly, subsequent signal processing to de-correlate the three dimension of signals will suppress the large scale signals from the large scale motions.

Alternate ways of suppressing/filtering the large scale signals, due to the large scale motions of a user, out from the desired signal may also be used. The electronic signals may be analyzed and then classified/identified as small signals and large signals which are separated out from the small signal amplitude of the micro-motions. The analysis may be of the form described in "Time Series Classification Using Gaussian Mixture Models of Reconstructed Phase Spaces" by Richard J. Povinelli et al., IEEE Transactions on Knowledge and Data Engineering, Vol. 16, No. 6, June 2004. Alternatively, a separation of the large signals due to voluntary motion may be made by using a BMFLC-Kalman filter as is described in "Estimation of Physiological Tremor from Accelerometers for Real-Time Applications" by Kalyana C. Veluvolu et al., Sensors 2011, vol. 11, pages 3020-3036, attached hereto in the appendix.

The magnified hand acceleration waveform 900T is more representative of an acceleration signal that includes tremors from which a micro-motion (micro-acceleration) signal of interest may be generated. The waveform 900T has a number of frequency components that are outside the frequency range of interest. For example, the frequency range of interest in the signal is from 8 Hz to 12 Hz, and/or from 8 Hz to 30 Hz. These frequency ranges are associated with known tremors that more human beings should commonly have.

Figure 11A:
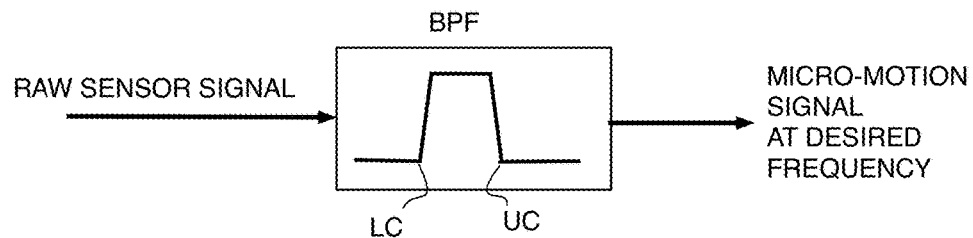
FIG. 11A is a functional block diagram of a band-pass filter to filter out signals outside the frequency range of a desired tremor to capture micro-motion signals.

Referring now to FIG. 11A, a band pass filter (BPF) is shown having a filter response with a lower cutoff (LC) frequency and an upper cutoff (UC) frequency at the ends of the desired frequency range. The BPF is in the form of a digital finite impulse response (FIR) band pass filter to filter a digital signal. This BPF will filter out undesirable frequency signal components from the raw electronic signal captured by the sensor to generate a micro-motion acceleration signal of interest in the desired frequency range. Three BPFs may be used in parallel, one for each axis signal. Alternatively, one BPF may be time shared between each axis.

Figure 11B:
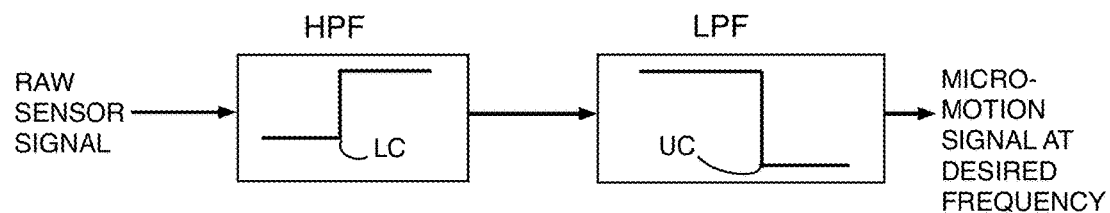
FIG. 11B is a functional block diagram of a high pass filter and a low pass filter to achieve the same results of the band pass filter of FIG. 11A.

Referring now to FIG. 11B, a digital high-pass filter (HPF) with the LC frequency and a digital low-pass filter (LPF) with the UC frequency can be combined in series to achieve a similar result to the digital FIR band pass filter in the generation of the micro-motion acceleration signal of interest. Alternatively, a low-pass filter with the UC frequency and a high-pass filter with the LC frequency can be combined in series to achieve a similar resultant signal output.

Additional signal processing are to be performed with the processor on the micro-motions signal to generate the NFP.

Gravity Correction for Accelerometer Sensor

It is desirable to remove the influence of the force of gravity on the three-dimensional accelerometry data captured by the accelerometer. This is so the NFP that is generated is substantially independent of device orientation. A dedicated three-dimensional touch pad sensor may not be influenced by the force of gravity. In which case, these steps need not be followed for three-dimensional data that is captured by a touch pad sensor when a user finger is touched against it.

The acceleration of gravity is a constant. Accordingly, the influence of the gravitation force is on the frequency spectrum is expected to be a fixed vector near zero frequency. The gravitation force acts as a zero frequency DC component so one would expect it would effectuate a leakage towards low frequencies in the signals (below 1 Hz).

Figure 12A:
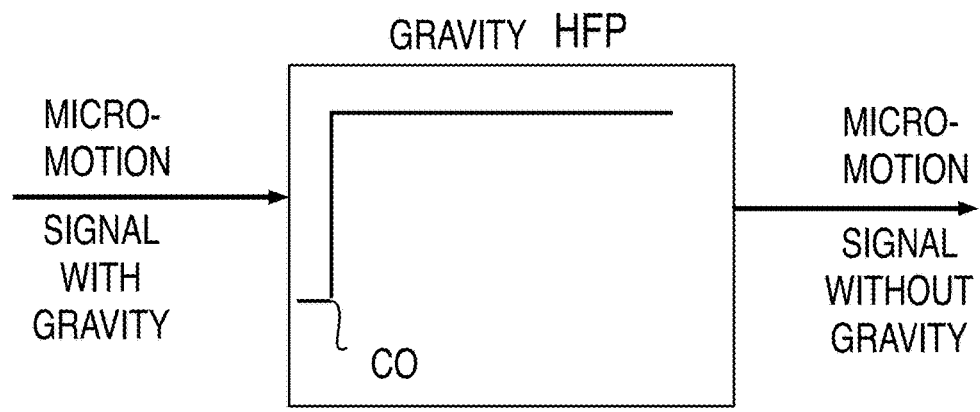
FIG. 12A is a functional block diagram of a gravity high-pass filter to filter the influence of gravity.

Referring now to FIG. 12A, a high pass filter at a cutoff frequency below 1 Hz (e.g., 0.25 Hz) may be used to compensate for the force of gravity and improve the accuracy of the recognition with an NFP. A micro-motion signal with the effects of gravity are coupled into the gravity high pass filter (HPF) having a high pass filter response with a cutoff (CO) frequency less than 1 Hz but greater than zero Hz. The signal output from the gravity HPF is the micro-motions signal without the effects of gravity.

Figure 12B:
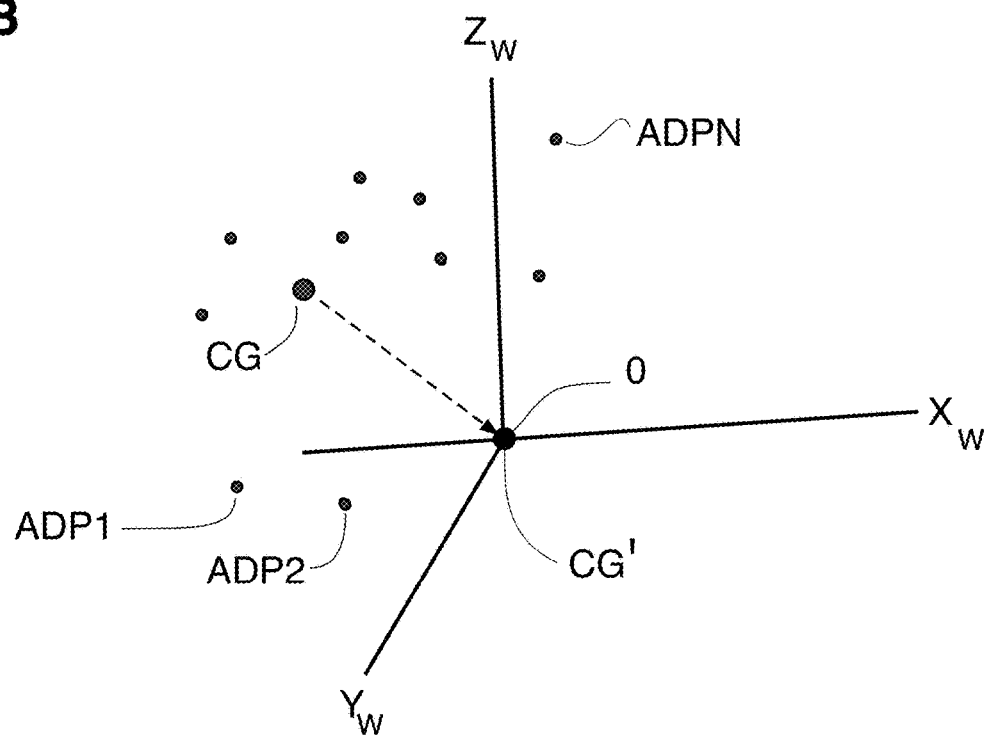
FIG. 12B is a diagram illustrating a coordinate transformation of data samples in a data set to move a center of gravity to the origin of the three axes to eliminate the influence of gravity.

Referring now to FIG. 12B, another way to eliminate the influence of the gravitation force is by transforming the coordinates of the 3D acceleration data points (ADP1-ADPN) each data set. The XYZ coordinates for the center of gravity CG in the sampled datasets of 3D acceleration points (X, Y, Z signals) over the predetermined sample period is first determined. Then, the coordinates of the 3D acceleration points in the given dataset undergo a translation transform so that the center of gravity is at the (X=0,Y=0,Z=0) coordinate or origin point of axes. The whole dataset undergoes a translation transform in this case.

Yet another way to get rid of the influence of the gravitation force in the acceleration signals would be to analytically correct a gravitation force vector for the phase shift that it induces in the 3D accelerometry data. The gravitation force vector can be determined from the raw 3D acceleration signals. Then, the 3D accelerometry data can be dampened in one direction in response to the gravitation force vector and strengthened in the opposite direction of the gravitation force vector.

Filtered Micro-Motions Waveform

After the filtering and suppression to remove unwanted signal and transformation to compensate for gravity or correlation, the desired micro-motions signal is formed.

Figure 13A:
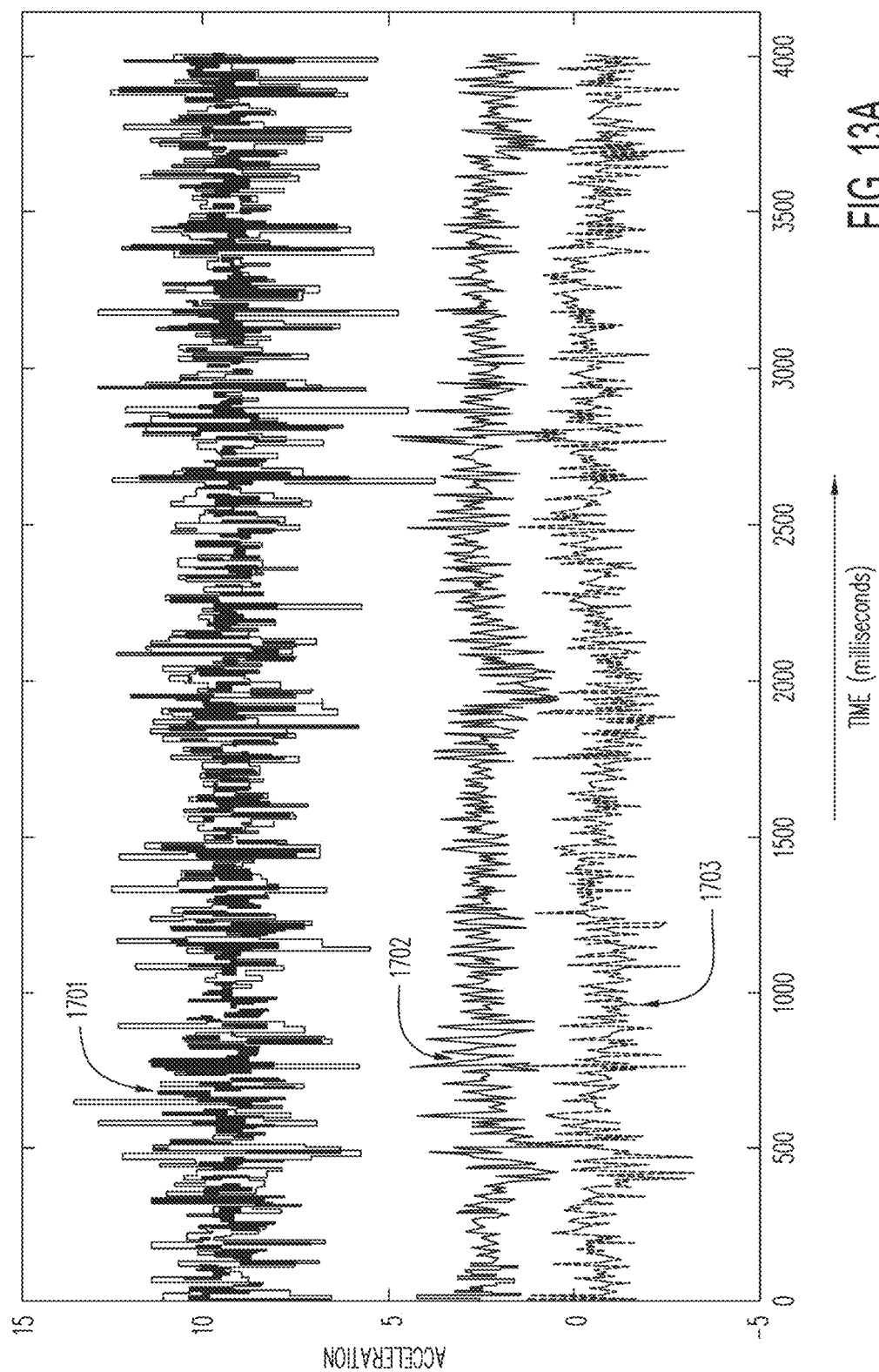
FIG. 13A is a waveform diagram of a raw unfiltered sample set of acceleration data signals in three dimensions from a 3D accelerometer.
Figure 13B:
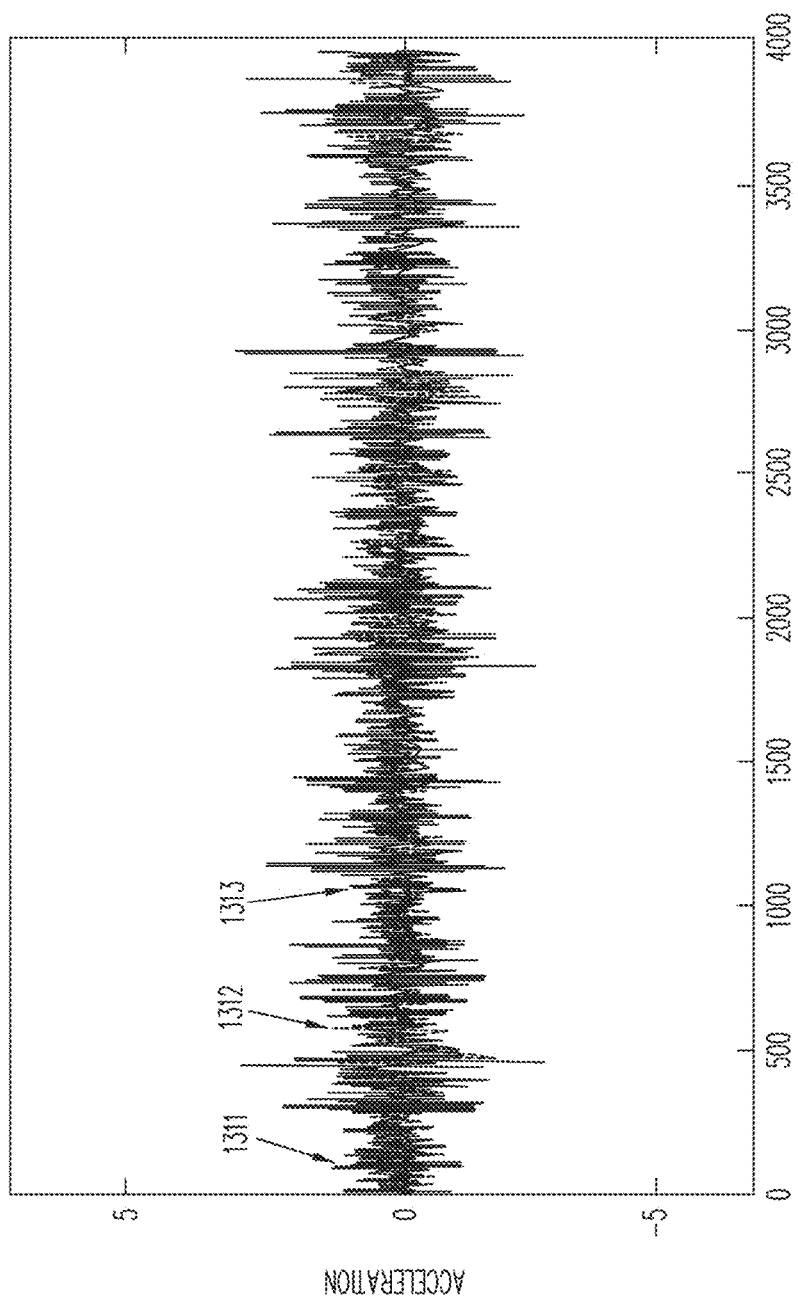
FIG. 13B is a waveform diagram of a 3-D micro-motions signal after preprocessing, band pass filtering, and gravity compensation of the raw signal waveforms shown in FIG. 13A.

Referring now to FIG. 13A, a waveform diagram shows three axes of raw acceleration waveform data 1301-1303 that are offset from each other due to gravitation forces and differences in orientation. FIG. 13B illustrates acceleration waveform data for three axes after suppression/removal/filtering of unwanted signals from the captured acceleration sensor data. The acceleration waveform data in FIG. 13B is representative of the micro-motions signal waveforms. If a 3D touch sensitive sensor is used instead of a 3-D accelerometer, a displacement waveform in three axes may be the resultant signal. While FIGS. 13A-13B show a sample of four seconds, sample periods of more or less time may be used.

There are three axis for the micro-motions signal corresponding to the three axis of acceleration sensed by the 3D accelerometer or the three axis of displacement sensed by the 3D touch pad sensor. The three axis of the micro-motions signal define points in three dimensions x(t), y(t), z(t) that can be plotted. The three dimensions of micro-motion signals x(t), y(t), z(t) over the sample period of time for a user can be further processed into phase(t), y(t), z(t) and plotted in a three-dimensional Poincare phase plot diagram such as shown in FIGS. 2A-2C.

The three-dimensional Poincare phase plot diagrams for the different users show that the micro-motion signals have unique patterns that can be used to identify and authenticate a user. A unique pattern for each user can be obtained from the Poincare phase plot diagram. Another unique pattern for each user could be obtained from the time series of the micro-motions themselves, without any phase information. However, it is easier to use a signal processor and digital signal processing algorithms to extract a unique pattern from the signal itself.

NFP Authentication Controller

Referring now to FIG. 14A, a block diagram of an NFP authentication controller 810 is shown. The NFP authentication controller 810 includes a signal processing and feature extractor module 1401 (may be split into two separate modules), an NFP authentication classifier module, and an authorization controller module 1404. The NFP authentication controller 810 may further include an optional secondary authentication module 1406 for multifactor authentication, such as by a keypad. One or more of the modules may be implemented by software/firmware instructions executed by a processor, hardwired electronic circuits, or a combination of each.

The NFP authentication controller 810 may further include a non-volatile storage device 1454 coupled to the classifier 1402 and the authorization controller 1404 to store data such as user calibration parameters 1466; access match (AM) level 1456A, mandatory recalibration (MR) level 1456B, voluntary recalibration (VR) level 1456C (collectively referred to as match percentage levels 1456); and an authentication enable bit (EN) 1455. Alternatively, the non-volatile storage device 1454 may be external to the NFP authentication controller 810 but remain internal to the electronic device as a secured independent non-volatile storage device or a secured part of a larger non-volatile storage device.

The NFP authentication controller 810 receives the three dimensions of the micro-motions data samples 1450 in each data set for each sample period. The micro-motions data samples 1450 are coupled into the signal processing and feature extractor module 1401. The signal processing and feature extractor module 1401 performs signal processing and signal analysis on the micro-motions data samples 1450 to extract a plurality of extracted features 1460X,1460Y, 1460Z for each of respective the three dimensions (X, Y, Z). The extracted features 1460X,1460Y,1460Z collectively represent the NeuroFingerPrint (NFP) 1460 that is coupled into the NFP authentication classifier module 1402.

The NFP authentication classifier module 1402 receives the NFP 1460, the extracted features from the micro-motions data samples 1450, and generates a match percentage (MP) signal output 1465. In a user mode, the match percentage signal 1465 is coupled into the authentication controller 1404. In a calibration or training mode, the match percentage signal 1465 is used by a processor in the electronic device to evaluate the match percentage signal 1465 in response to selections for the initial user calibration parameters 1466. It is expected that training/calibration of the NFP authentication classifier module and the generation of the initial user calibration parameters 1466, last between 5 and 10 seconds. It is expected that in the user mode, that it take less than 5 seconds to sense motion in a body part of a user and determine that access be granted or denied.

In the calibration or training mode, an authorized user may generate one or more sets of user calibration parameters 1466 so that the NFP authentication system operates under different conditions. For example, a user may want to hold the electronic device in either hand and have access granted. The tremors will be different between left and right hands or between different fingers. The user may want to calibrate the NFP authentication system to both left and right hands or to a plurality of fingers. Moreover, in some cases, more than one user will be using an electronic device. In which case, multiple individuals may be authorized users and multiple calibrations will need be made and stored. Thus, the storage device 1454 may store a plurality of sets of user calibration parameters for the same authorized user or different authorized users.

The authentication enable bit (EN) 1455 is coupled into the authentication controller 1404. The authentication enable bit (EN) 1455 may be used to enable the authentication controller 1404, subsequent to the initial calibration or training mode. After initial calibration or training mode, the authentication enable bit (EN) 1455 is set and the authentication controller 1404 is enabled. The authentication enable bit (EN) 1455 is not reset in the user mode or a recalibration mode after the initial calibration or training mode. Unless the entire electronic device is erased, along with the enable bit, the authentication controller 1404 is enabled by the enable bit 1455 for enhanced security.

In the user mode, the match percentage signal 1465 is used by the authentication controller 1404 to evaluate whether or not to grant access into the electronic device and its software applications. The match percentage signal 1465 is evaluated against the access match level 1456A to generate the access granted (AG) signal 1499. If the match percentage signal 1465 is greater than or equal to the access match level 1456A, the access granted (AG) signal 1499 is generated at a logic level to signal access is granted. If the match percentage signal 1465 is less than the access match level 1456A, the access granted (AG) signal 1499 is not generated and access is not granted. The access granted (AG) signal 1499 is coupled to the processor in order to enable the authorized user to control and operate the functions of the electronic device.

If the optional secondary authentication module is used, a secondary match (SM) signal 1468 is coupled into the authentication controller 1404. In this case, the authentication controller 1404 further evaluates the secondary match signal 1468 on whether or not to generate the access granted (AG) signal 1499. The authentication controller 1404 may use AND logic to require two conditions be met before the access granted signal is generated. Alternatively, the authentication controller 1404 may use OR logic to require two conditions be met before the access granted signal is generated.

In response to an inactive reactivate signal 1470 from the processor, the authentication controller 1404 maintains the access granted signal 1499 in an active state for so long as the user uses the electronic device and avoids a sleep state or a time out to enter a protected state. If the sleep state or time out occurs, the reactivate signal 1470 is pulsed by the processor. In response to the pulsed reactivate signal, the authorization controller 1404 inactivates the access granted signal 1499 so that a user must re-authenticate himself/herself with the NFP authentication system of the electronic device to gain access.

Figure 15:
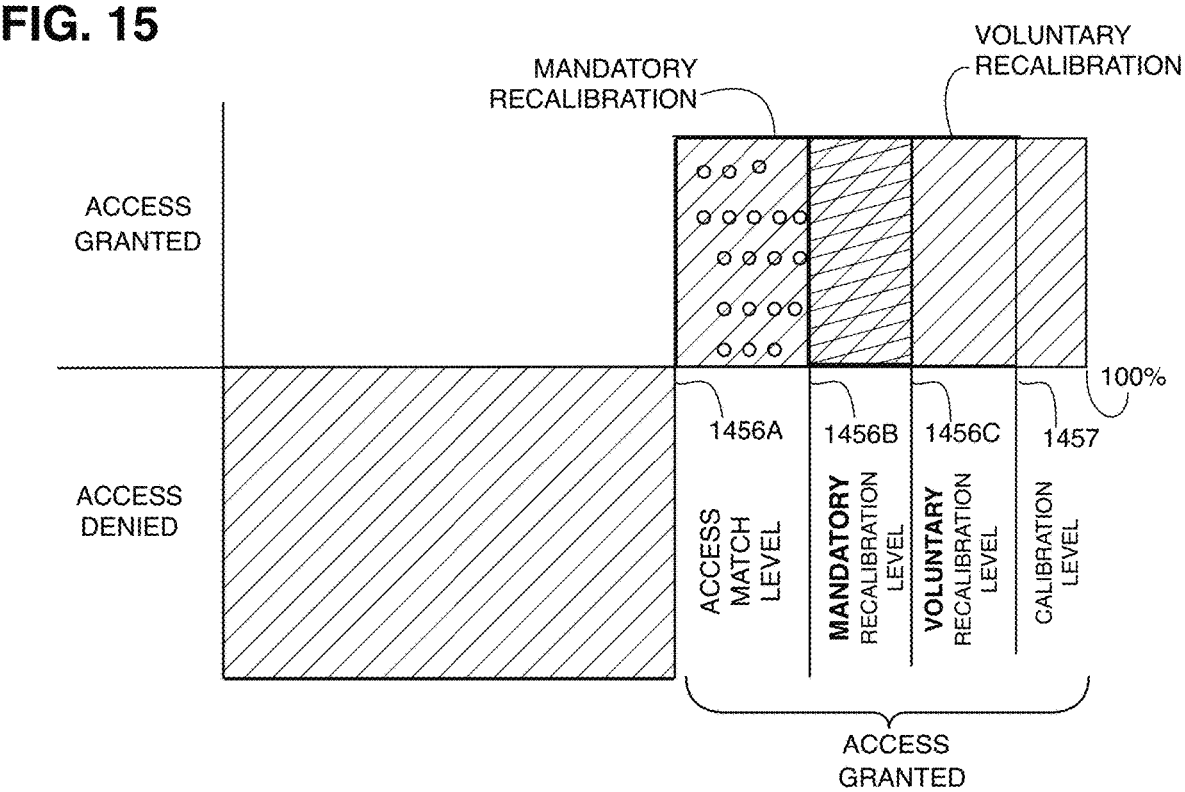
FIG. 15 is a graph of access and recalibration control by the authentication controller shown in FIG. 14A.

Referring now to FIG. 15, a graph of match percentage levels (MP) 1456 is shown in comparison with the match percentage signal 1465 along the X axis. The Y axis indicates the generation of the access granted (AG) signal 1499 by the authentication controller 1404 and whether or access is to be granted to an alleged user.

In the user mode, the match percentage signal 1465 is used by the authentication controller 1404 to evaluate whether or not to grant access into the electronic device and its software applications. The match percentage signal 1465 is evaluated against the access match level 1456A. If the match percentage signal 1465 is at or above the access match level 1456A the access granted (AG) signal 1499 is generated by the authentication controller 1404. If the match percentage signal 1465 is below the access match level 1456A, the access granted (AG) signal 1499 is not generated by the authentication controller 1404.

Referring now to FIGS. 14A and 15, the authentication controller 1404 may also generate one or more recalibration signals to inform the user to recalibrate the NFP authentication system by regenerating the user calibration parameters 1466 for the authorized user, before the NFP authentication classifier 1402 fails to generate a level of the match percentage signal 1465 at or above the access match level 1456A.

In the training or calibration mode, the NFP authentication classifier 1402 is trained/calibrated by initial user calibration parameters 1466 so that the NFP authentication classifier 1402 generates a level of the match percentage signal 1465 at a calibration level 1457 that may be at or near 100%, such as 98%. After training, in the user mode, the NFP generated by a user over time can shift as his/her body ages, disease, or other reason that affects the physiological condition of the body. Accordingly, the match percentage signal 1465 may decrease from the calibration level 1457 as time passes. Periodic recalibration is used to reset the user calibration parameters 1466 so that the match percentage signal 1465 is brought back to the calibration level 1457. Periodic recalibration may be required more or less often of a user depending upon the user's age, health, and other physiological conditions of the body.

In the user mode, the NFP authentication classifier 1402 is used by the authentication controller 1404 to evaluate whether or not recalibration is needed. The determination of recalibration is responsive to the mandatory recalibration (MR) level 1456B and the voluntary recalibration (VR) level 1456C. The mandatory recalibration (MR) level 1456B is less than both the voluntary recalibration (VR) level 1456C and the calibration level 1457. The voluntary recalibration (VR) level 1456C is less than the calibration level 1457.

Recalibration requires that the user first be verified as an authorized user, access must be first granted to the electronic device to enter the user mode and recalibrate. If the device is stolen by an unauthorized user, the unauthorized user will not be granted access to recalibrate the device.

If the match percentage signal 1465 falls below the voluntary recalibration (VR) level 1456C, a voluntary recalibration signal 1471 is generated by the authentication controller 1404. In this case, the electronic device informs the user through its user interface, that he/she should pause and take a moment to voluntarily recalibrate the NFP authentication system by regenerating the user calibration parameters 1466. It is expected that most users would voluntarily choose to recalibrate the NFP authentication system. However, there will be some authorized users who will choose to wait, forget the warning, or ignore it entirely.

For those authorized users that do not voluntarily recalibrate the NFP authentication system, they may be forced to undergo a mandatory recalibration process. If the match percentage signal 1465 further decreases and falls below the mandatory recalibration (MR) level 1456B, a mandatory recalibration signal 1472 is generated by the authentication controller 1404. In this case, after the authorized user is verified by the NFP authentication classifier 1402 and granted access by the authentication controller 1404, the electronic device immediately goes into a recalibration mode informs the user through its user interface to prepare and perform the recalibration procedures by continuing to hold the device appropriately or touch a button appropriately. The user is further informed that the NFP authentication system is performing recalibration and to wait until the recalibration is completed and the NFP authentication system has been successfully recalibrated with the regeneration of the user calibration parameters 1466 to generate the match percentage signal 1465 at or above the calibration level 1457.

If the electronic device is not used for some time, it is possible that the match percentage signal 1465 further decreases and falls below the access match (AM) level 1456C. In which case, the authorized user may be denied access. Accordingly, selection of the value for the access match (AM) level 1456C is important so that the authorized users are not readily denied access to the electronic device while unauthorized users are denied access. It is desirable to make the generation of the NFP signal 1460, generated by the module 1401 and coupled into the NFP authentication classifier 1402, less sensitive to variances of a user (e.g., time-aging, disease) so that the recalibration is less frequent. Accordingly, it is desirable to select signal processing and feature extraction algorithms of the module 1401 so that the sensitivity in the generation of the NFP is low and it is less likely to change over time.

Example settings of the match percentage levels (MP) 1456 in increasing order is 85% for the access match (AM) level 1456A, 90% for the mandatory recalibration (MR) level 1456B, and 95% for the voluntary recalibration (VR) level 1456C. Thus, a user is informed by the user interface of the electronic device to perform a voluntary recalibration before being required to perform a mandatory recalibration.

With the mandatory recalibration being required of the user, it should avoid the NFP authentication system from denying access to the electronic device if it is being actively used. If the electronic device sits for some time (e.g., one or more years), a user may be required to wipe the electronic device clean, re-initialize the NFP authentication system, and reload applications and/or data, such as from a backup.

Figure 14B:
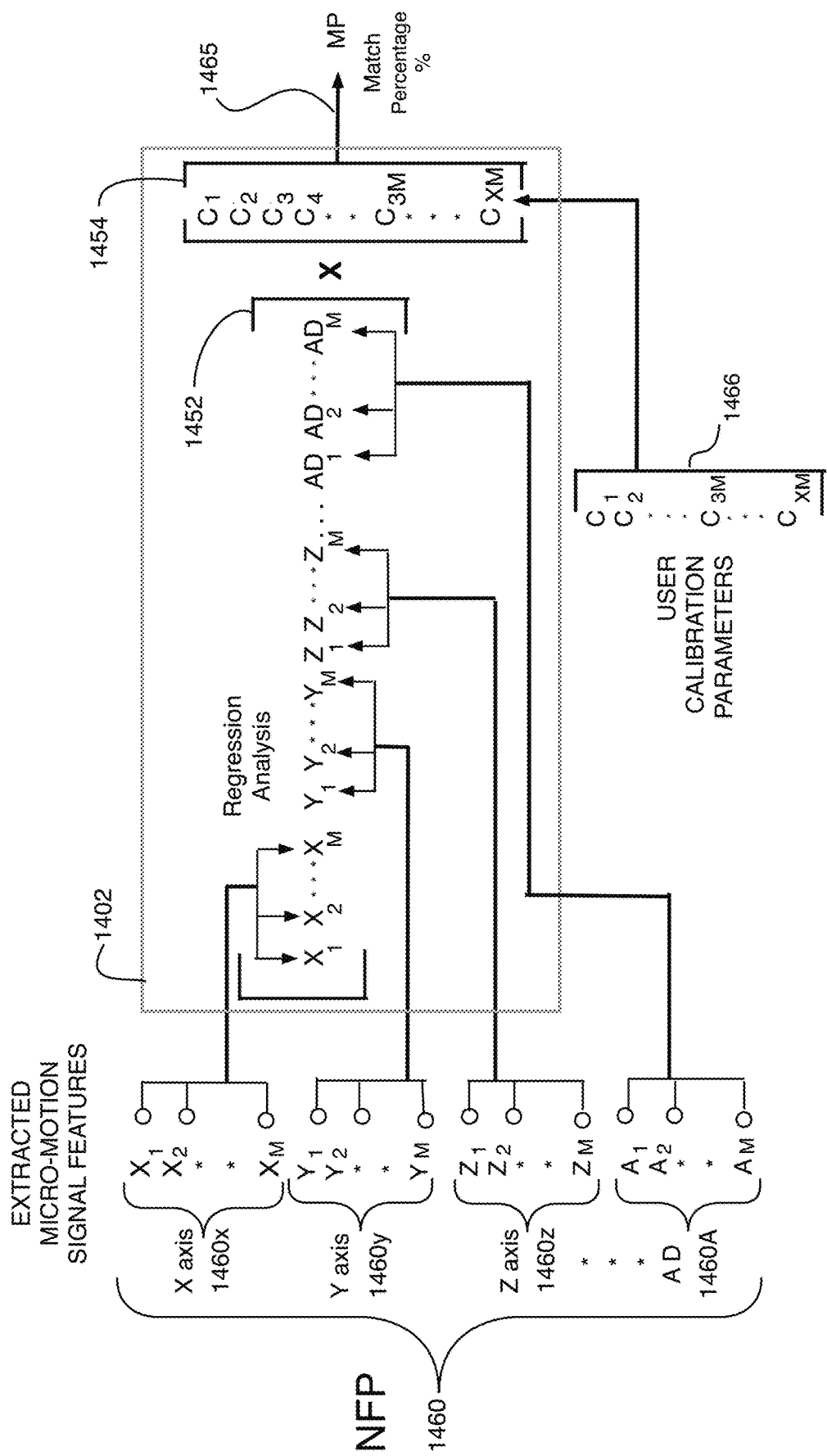
FIG. 14B is a functional block diagram of the NFP authentication classifier shown in FIG. 14A

Referring now to FIGS. 14A-14B, a model for an NFP authentication classifier 1402 is shown. The model is a regression analysis model that may be linear in accordance with one embodiment. In alternate embodiment, the regression analysis model for the NFP authentication classifier 1402 may be non-linear. During a training or calibration mode, features of the micro-motion signals from an authorized user are extracted by the signal processing and feature extraction module 1401 to generate a calibration NFP 1460, including calibration NFP information 1460X,1460Y,1460Z for each axis.

The calibration NFP information 1460X,1460Y,1460Z for each axis is placed into a single row NFP matrix 1452. Appropriate values of authorized user calibration parameters 1466 are unknown. The values for user calibration parameters 1466 can be randomly set into a single column calibration matrix 1454. Matrix multiplication is performed by the processor to multiply the single row NFP matrix 1452 and the single column calibration matrix 1454 together to get a match percentage value 1465.

During calibration/training, the processor searches out the user calibration parameters 1466 that are to be placed in the single column calibration matrix 1454 to generate a predetermined value for the match percentage 1465. This predetermined value is referred to as the calibration level 1457. For example, the calibration level 1457 may be set to 90%. In which case, the processor searches out values for the authorized user calibration parameters 1466 such that when multiplied with the NFP 1460, the match percentage 1465 output from the classifier is 90% or greater.

Once the authorized user calibration parameters 1466 are set and stored in the electronic device, the NFP classifier 1402 uses the authorized user calibration parameters 1466 to multiply against subsequent regenerated NFPs that are generated from an unknown user or the authorized user.

If a person cannot subsequently generate a regenerated NFP that is substantially similar to the calibration NFP, when the user calibration parameters 1466 are multiplied against a differing regenerated NFP, the value of the match percentage 1465 generated by the classifier 1402 will be low. The authorization controller 1404 can be set so that low values for the match percentage 1465 deny access to unknown persons who generate a significantly different regenerated NFP.

If a person subsequently generates an NFP, a regenerated NFP that is substantially similar to the calibration NFP, when the user calibration parameters 1466 are multiplied against the regenerated NFP, the value of the match percentage 1465 generated by the classifier 1402 will be high. The authorization controller 1404 can be set such that high values for the match percentage 1465 above an access match level 1456A grants access to an electronic device.

Signal Processing and Feature Extraction to Generate NFPs

Referring now to FIG. 13A, a raw unfiltered sample of acceleration data in three dimensions from a 3D accelerometer is shown. For X, Y, and Z axes of the electronic device, raw signals 1301-1303 are captured for each of the three dimensions. With some preprocessing, band pass filtering, and compensation for gravity, micro-motion signal waveforms 1311-1313 shown in FIG. 13B can be respectively formed from the raw signals 1301-1303. Further signal processing can then be performed on the micro-motion signal waveforms 1301-1303 to form an NFP for the given sample of acceleration data. There are various ways to generate an NFP from the micro-motions signal. Once calibrated/trained, the NFP authentication controller in an electronic device uses a consistent method of generating the NFP.

The micro-motion signal in three dimensions is related to a common tremor that is found in users. There is a pattern hidden in the time domain of the micro-motions signal that is unique to each user as it is originating in his/her neuro-muscular functioning. It is desirable to emphasize the pattern by performing signal processing on the micro-motions signal and then extracting features therefrom to form an NFP. A calibration NFP can then be used to generate authorized user calibration parameters during a training or calibration process. The authorized user calibration parameters can be subsequently used to classify regenerated NFPs and distinguish the known authorized user from unknown unauthorized users for the purpose of user authentication.

However, before an NFP can be used for authentication, it is used to train or calibrate a model of a classifier by generating a set of authorized user calibration parameters. This set of authorized user calibration parameters are then subsequently used with the classifier model to evaluate future NFPs (regenerated NFPs) that are captured by sensors from unknown persons. Various signal processing algorithms can be used to extract data from the micro-motions signal as the NFP.

Hidden patterns in the micro-motions signal, such as the micro-motion signals waveforms 1311-1313 shown in FIG. 13B for example, may be detected with an inverse spectral analysis. The inverse spectral analysis is performed in order to recover unknown signal components linked to time variance.

One type of inverse spectral analysis that may be used is a Cepstrum analysis. Cepstrum analysis is a tool for the detection of periodicity in a frequency spectrum. It can be used to detect repeated patterns, their periodicities, and frequency spacing.

Generally, a CEPSTRUM is the result of taking the Inverse Fourier transform (IFT) of the logarithm of the estimated spectrum of a signal.

As shown by the equation below, a power CEPSTRUM of a signal may be defined as the squared magnitude of the inverse Fourier transform of the logarithm of the squared magnitude of the Fourier transform of a signal.

Figure 16:
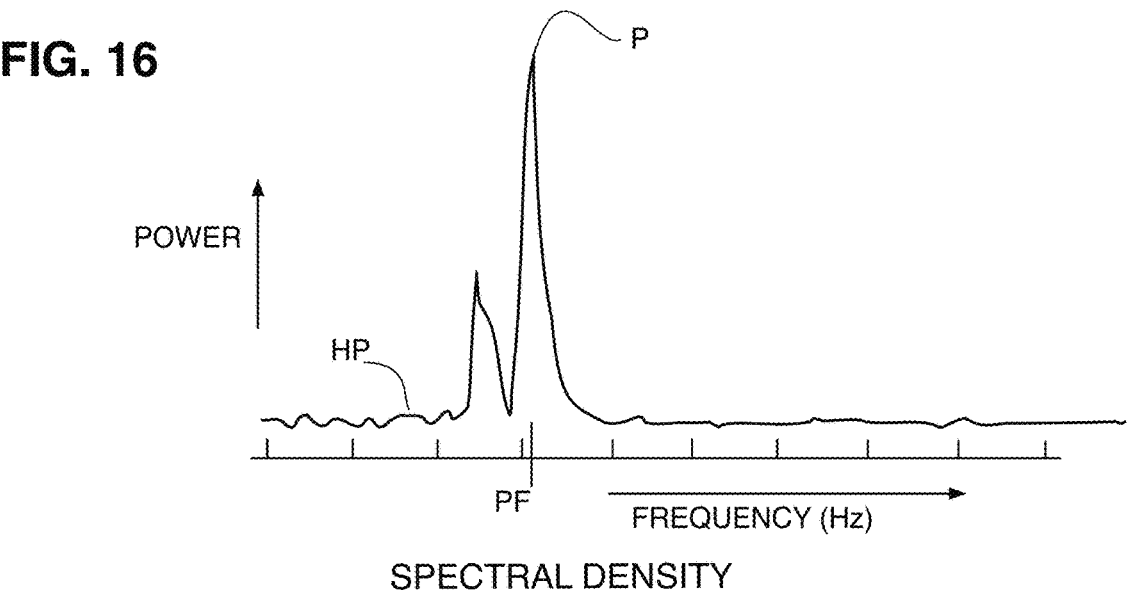
FIG. 16 is a plot of power spectral density in a micro-motions signal associated with a tremor.

Power CEPSTRUM of signal=$|\mathcal{F}^{-1}\{\log(|\mathcal{F}\{f(t)\}|^2)\}|^2$ Initially, a Fourier spectrum of the micro-motions signals, such as the micro-motions signals shown in FIG. 13, is taken using a Fast Fourier transform. Mathematically this may be accomplished by performing a Fourier Transform using the equation $\hat{f}(\xi) = \int_{-\infty}^{\infty} f(x) e^{-2\pi i x \xi} dx,$ where ξ represents real frequency (in hertz) values and the independent variable x represents time), the transform variable. Using software or digital circuits that can digitally sample a signal, a discrete-time Fourier Transform (DFT) may be used represented by the equation $X_k = \sum_{n=0}^{N-1} x[n] \cdot e^{-i 2\pi \frac{kn}{N}}.$ The result of Fourier transform on the micro-motions signal is the spectral density (power spectrum or Fourier spectrum). FIG. 16 illustrates an example of a spectral density taken on acceleration over time for a tremor at the hand. Note that the expected peak (P) signal component of a physiological tremor is at a peak frequency (PF) of around 10 to 12 Hz. However, there is still much hidden pattern (HP) information in the spectra density curve for the tremor that is useful.

The spectral density (power spectrum) is a composite of the component frequencies of a signal. That is, there are numerous signal frequencies that are composed together to form the spectral density curve. It is desirable to effectively separate them out to show a pattern. The composite of signals illustrated by the spectral density is a convolution of signals equivalent to multiplications of the constitutive signals.

Taking the logarithm of a convolution effectively turns it into a summation of the constitutive signals instead of a multiplication. Additionally, a logarithm of the spectral density (or a logarithm of the square of spectral density) emphasizes the lower amplitude frequency components in the spectra density curve where hidden pattern (HP) information may be found. Taking a logarithm of the spectral density effectively compresses the large signal amplitudes in the spectral density signal and expands the smaller amplitudes in the spectral density signal.

However, it is difficult to see the periodicity and patterns in the signal waveform generated by a logarithmic transform. Accordingly, an inverse Fourier transform (IFT) is performed on the logarithm signal waveform so that the unknown frequency component and hidden patterns are visible. The inverse Fourier transform of the logarithmic transform separates the components of the composite signal in the spectra density of the micro-motions signal waveforms.

Figure 17A:
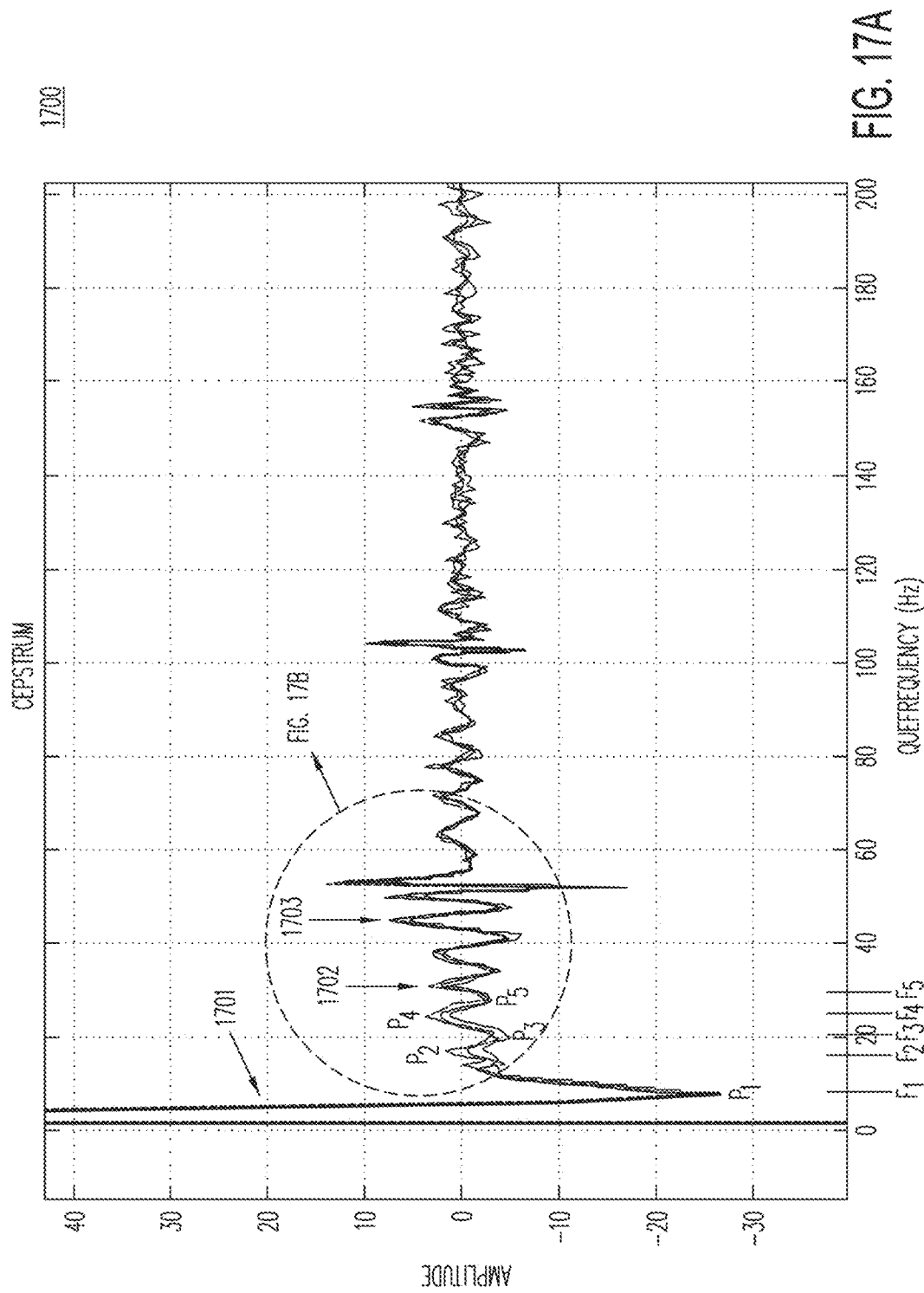
FIG. 17A is a plot of a CEPSTRUM waveform generated by performing a CEPSTRUM analysis on the micro-motions waveform shown in FIG. 13B.
Figure 17B:
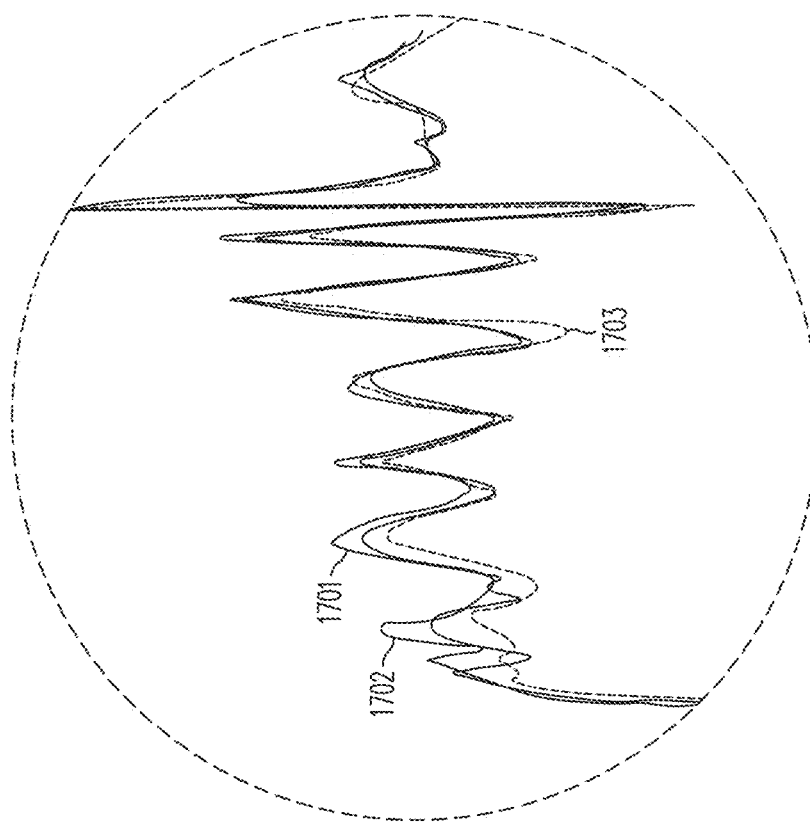
FIG. 17B is a magnified view of a portion of the plot of the CEPSTRUM waveform shown in FIG. 17A.

FIGS. 17A-17B illustrate a CEPSTRUM taken on the micro-motions waveforms shown in FIG. 13B. This resultant waveform that is generated after taking the inverse Fourier transform (IFT) of the Log of the spectrum. The CEPSTRUM generates a substantially resolved series of the unknown signal components in the resultant waveform. Values for a pattern of features can be extracted from each axis (dimension) in the resultant waveform and used as an NFP to identify a user. Note that the horizontal axis of the CEPSTRUM waveform shown in FIGS. 17A-17B is quefrency and not a measure of time in the time domain.

Generally, the inverse Fourier transform is an integral that can integrate a function g over values of its variable. The inverse Fourier transform in this case may be represented by the equation:

$\mathcal{F}^{-1}g(x) := \int_{\mathbb{R}^e} e^{2\pi i x \cdot \xi} g(\xi) d\xi,$ To recover a discrete time data sequence x[n], an inverse discrete Fourier transform (IDFT) may be used.

$x[n] = T \int_{\frac{1}{T}} X_{1/T}(f) \cdot e^{i 2\pi f n T} df$ (integral over any interval of length $1/T$)

$= \frac{1}{2\pi} \int_{2\pi} X_{2\pi}(\omega) \cdot e^{i\omega n} d\omega.$ (integral over any interval of length $2\pi$)

Using an Inverse Fast Fourier Transform (IFFT) the equation becomes $IFFT_N(n, F) = \sum_{k=0}^{N-1} F(k) e^{+j 2\pi n k/N} = \sqrt{N} f(n)$ where a sequence of N samples f(n) are indexed by n=0 to N−1, and the Discrete Fourier Transform (DFT) is defined as F(k), where k=0 to N−1.

$F(k) = \frac{1}{\sqrt{N}} \sum_{n=0}^{N-1} f(n) e^{-j 2\pi k n/N}$

FIGS. 17A-17B illustrate an example of a three dimensional CEPSTRUM waveform signal 1700. The waveform and signal 1700 is the result of performing a CEPSTRUM analysis on the micro-motions signal resulting in CEPSTRUM signal waveforms 1701,1702,1703, one for each dimension in the micro-motions signal. The CEPSTRUM waveform signal 1700 has distinct features associated with it that can be readily used to identify a user. For example, the first N peaks of the CEPSTRUM waveform 1700 may the predetermined features to extract from each CEPTSTRUM waveform 1700 to identify a user. The peaks are chosen for their high variance so they are distinct features. For each user, the values of quefrency and amplitude for the first N peaks can be used as the respective user's NFP. The values of quefrency and amplitude for the N peaks are can be used as the NFP that is input into the classifier model to generate the match percentage (MP), in response to authorized user calibration parameters.

Other features can be selected and their values extracted from the CEPSTRUM of the micro-motions signal. Other signal processing may be performed so that additional features or patterns in the micro-motions signal become apparent and may be used in the generation of an NFP. Consistency in what features are used to extract values is key for an NFP authentication system. The features should be predetermined. The same features (e.g., first N peaks) should be used during a calibration/training mode with a calibration NFP and when in a use mode and forming the regenerated NFPs from new sample sets.

Figure 18A:
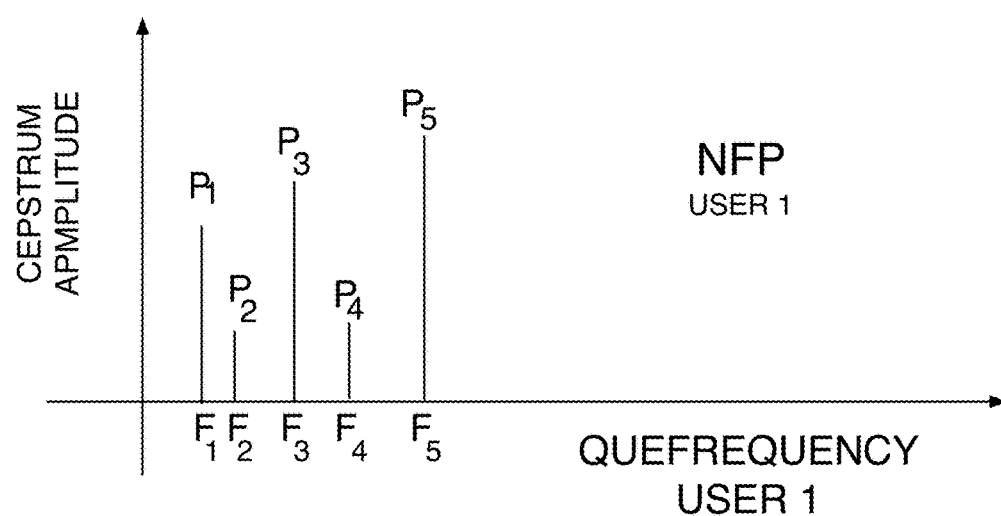
FIGS. 18A-18B illustrate examples of different NFPs for a single axis based on quefrency for two different users.
Figure 18B:
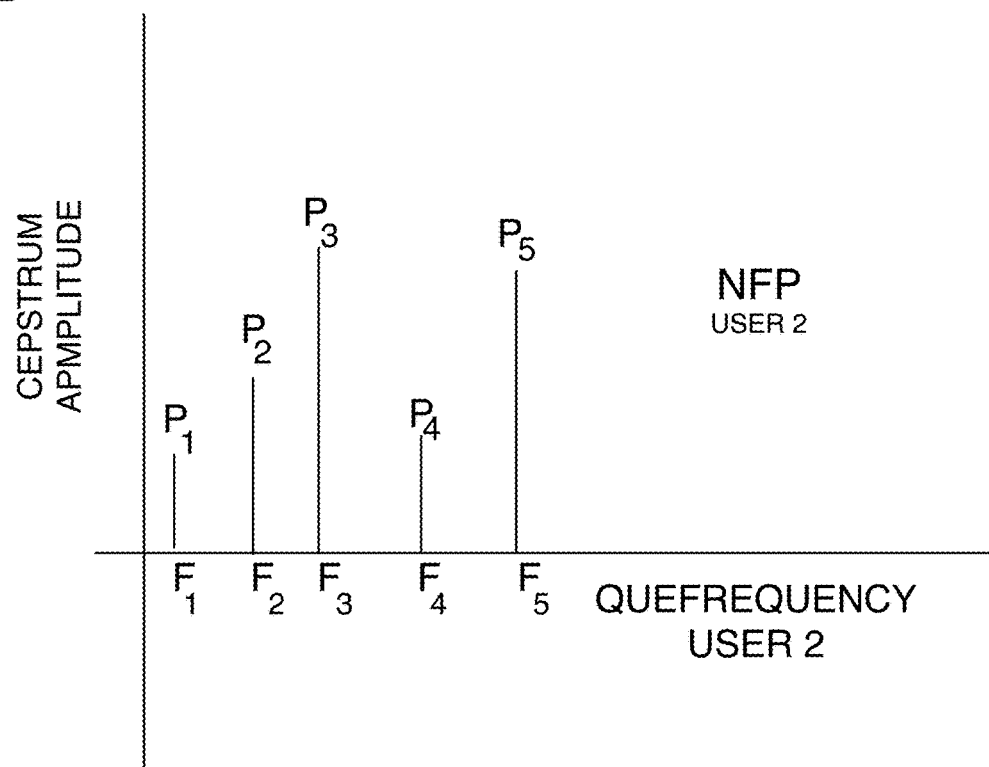

For example, in FIG. 17A it can be seen that the first five peaks P1, P2, P3, P4, P5 at their respective quefrequencies and amplitude on each axis (e.g., 3×5 total amplitude values from 3 axes/curves and 5 peaks) have a large variance that may be used to distinctly identify a user. The amplitudes and quefrencies for the first five peaks P1, P2, P3, P4, P5 will be significantly different when captured from a different user. Thus, the values of the amplitudes and quefrencies extracted for the first five peaks P1, P2, P3, P4, P5 can be used to distinguish the identity of users, such as shown in FIGS. 18A-18B for example. While the first five peaks are used in this example, it is not a constraint or a limitation on the embodiments as fewer peaks, additional peaks, or a plurality of other features may be selected to form NFPs.

With the first five peaks P1, P2, P3, P4, P5 being the predetermined feature used to extract values from the CEPSTRUM signal waveform, the NFP can be regenerated over and over again for the same user with minor variation. If a different user generates his/her NFP, the extracted values for the predetermined features will substantially vary. The substantial variance between NFPs of an authorized user and a different user can be used to grant access to the authorized user and deny access to the different user.

The first N features extracted from a CEPSTRUM waveform can be used to regenerate an NFP and used by the NFP authentication classifier to classify matches with authorized user calibration parameters. Selecting earlier features in the CEPSTRUM, such as the first N (e.g., N being 3 to 5) peaks or other coefficients, may decrease the sample period but still represent much of the variance in the signal. These first N coefficients can be expanded into 128 extracted features by projecting the N features by PCA analysis, and hence become linear combination of 128 extracted features, for example.

Over a sample period of 5, 10, or 20 seconds, the values extracted from the CEPSTRUM waveform are the positions (quefrencies) and their respective amplitudes of the predetermined feature. If the predetermined features are the first five peaks for example, the values of amplitude and quefrency for each axis are extracted as the NFP. This method aggregates time over a sample period.

Instead of aggregating time over the sample period, the CEPSTRUM may be analyzed in near-real time. In this case for example, one peak at one quefrency may be selected and plotted as a function of time. For example, peak P1 may be selected at a quefrency of 8 in FIG. 17A. The 3D coordinates for amplitude of each axis at the quefrency of 8 can then be plotted as a function of time. Other features at other quefrencies can be further selected so there are N frequencies (e.g., 128 'quefrencies') so an n-space analysis can be performed using a nearest neighbor, a linear or quadratic analysis where n is 128 for example.

However, an analysis of 128 quefrencies is a challenge. The analysis can be made simpler and ease computing time, by looking at where the most variance is in a waveform. We can take the first 3, 5, or 10 quefrequency positions and perform a principle component analysis (PCA) in 3, 5, or 10 dimensions of data space. A nearest neighbor analysis can then be performed, for example, on this restricted data space to extract values for the NFP.

Another way of feature extraction and generating values for the NFP can be done without 3D plotting of data points per quefrency as a function of time. One can take quefrency, amplitude and time as true coordinates of a vector. N quefrencies can be selected to plot amplitude and time as dimensions. These vectors can then be plotted for resolved frequencies at any given time. This generates a time-series of those extracted features that can be analyzed to extract values for the NFP.

Another way of feature extraction and generating values for the NFP is to extract those frequencies (quefrencies), amplitudes at various times (like 50 times a second remembering that the interesting and relevant raw signals are bandpassed between 16 and 30 plus Hz). Within a few seconds, a series of numbers are generated that may be used as extract values for the NFP. Values at different time points instead of quefrency may be extracted and used as the NFP.

While CEPSTRUM signal processing is described herein, other signal processing algorithms can be used on the micro motion signals so that other patterns appear in a different waveform. Different features can be extracted from that waveform signal and used to define an NFP for the NFP authentication classifier. The different extracted features can be used as the NFP that is input into a model to generate the match percentage (MP) in response to authorized user calibration parameters.

Referring now to FIGS. 18A-18B and 19A-19B, examples of a single axis of different NFPs for different users are shown. Additional dimensions may be provided by the two or more additional dimensions.

Figure 19A:
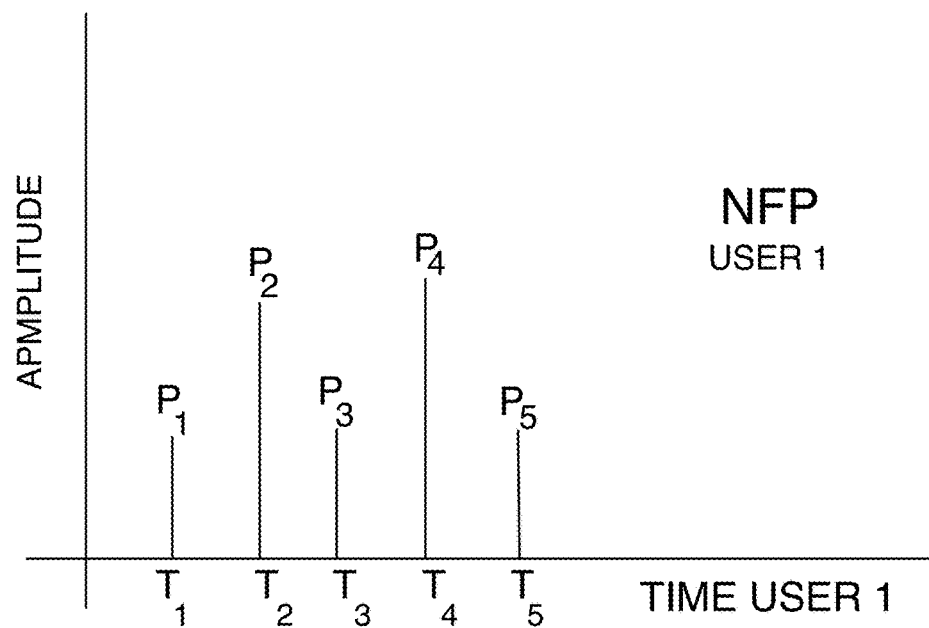
FIGS. 19A-19B illustrate examples of different NFPs for a single axis based on time for two different users.
Figure 19B:
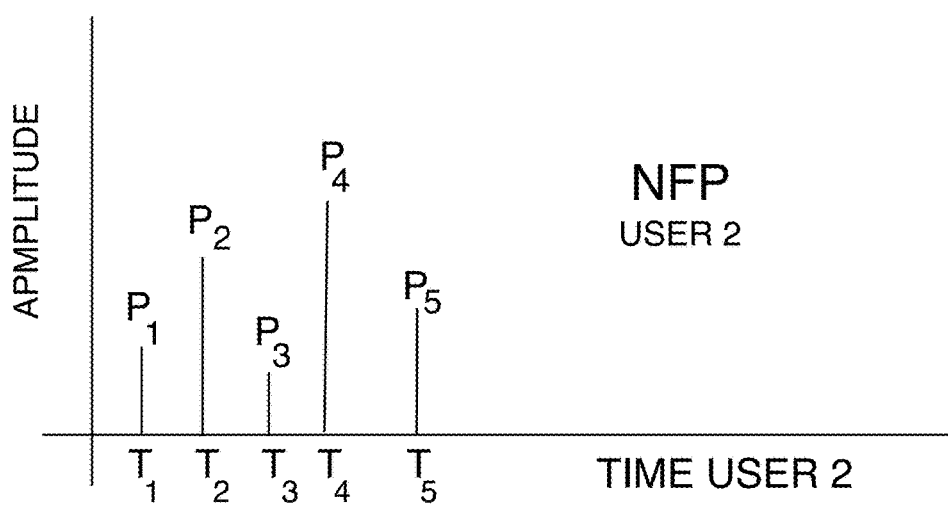

FIGS. 18A-18B illustrate examples of different NFPs for a single axis based on quefrency for two different users. One or more of the five extracted peaks P1-P5 occur at different quefrencies F1-F5 with different amplitudes in each of FIGS. 18A-18B. Accordingly, the NFP of each user differs. FIGS. 19A-19B illustrate examples of different NFPs for a single axis based on time for two different users. One or more of the five peaks P1-P5 occur at different times T1-T5 with different amplitudes in each of FIGS. 19A-19B. Accordingly, the NFP of each user differs.

The first five peaks of the CEPSTRUM signal waveform are the predetermined features to be extracted for each user from the different micro-motion signals of each user. The values for placement and amplitude of the first five peaks distinguish one user from another, similar to how teeth and cuts in a door key distinguish keys. The authorized user calibration parameters act somewhat like tumblers of a lock that engage the teeth and cuts in a door key. If the teeth and cuts in the door key are wrong, the tumblers of the door lock will not be properly engaged to unlock the lock. With more than one dimension (e.g., 3 axis) for feature extraction, the more unique the NFPs become. FIG. 14B illustrates an added dimension AD 1460A of values of features that are extracted over and above the three dimensions of features extracted from the micro-motions signal 1460X,1460Y, 1460Z to form the NFP 1460.

While the 3D acceleration or 3D displacement values may be used, time may be another dimension added. At one point in time, the 3D values with have one amplitude while at another point in time they will have another.

Training/Calibration

Referring now to FIG. 14B, one or more dimensions for an NFP 1460, and user calibration parameters (if trained) are coupled into the NFP authentication classifier 1402. The algorithm for the NFP authentication classifier is a data mining algorithm, such as a linear regression algorithm, a non-linear regression algorithm, a linear quadratic algorithm, a quadratic equation algorithm, a nearest neighbor classifier, or a k by N nearest neighbor classifier. A linear regression algorithm is shown with a one row matrix 1452 with xM elements or columns multiplied together with a one column matrix 1454 with xM rows. The one row matrix 1452 represents the NFP 1460 with its values for the extracted features for each of the one or more dimensions. The one column matrix 1454 represents the authorized user calibration parameters 1466. The multiplication in this case provides a value for a match percentage. During training/calibration, the user calibration parameters 1466 are adjusted to form a calibration level as the match percentage (MP) output 1465.

The NFP authentication classifier 1402 is trained/calibrated before use by an authorized user. Once the initial training/calibration is completed, unauthorized users cannot train or recalibrate the classifier 1402. Micro-motions signals are captured during one or more sample periods by the accelerometer with the electronic device in a user's hand or with the user pressing a touch sensor. The calibration may occur with left or right hands or both hands for an accelerometer. The calibration for a touch sensor may occur with one or more fingers of each hand.

The micro-motion signals are processed using signal processing algorithms and features are extracted out of the resultant waveform as NFP calibration samples, referred to herein as the calibration NFP. During training/calibration, the NFP calibration samples are used to find authorized user calibration parameters 1454 associated with the authorized user and train/calibrate the classifier to generate a desired calibration match percentage level. After the authorized user calibration parameters 1454 have been generated and securely stored away, the calibration NFP is discarded for security reasons. By not saving the calibration NFP, an NFP needs to be regenerated in the user mode, referred to as the regenerated NFP, for a user to gain access to the electronic device. After device authentication has been reenacted to lock the device from access, the NFP needs to be regenerated by the authorized user.

The regenerated NFP is generated with another sample of the neuro-mechanical micro-motions from the user and by recalling the stored authorized user calibration parameters from a storage device. The regenerated NFP is then used for authentication purposes to gain access to the electronic device. With the regenerated NFP, the authorized user calibration parameters are likely to provide a high match percentage such that access is likely to be granted once again to the electronic device. Like the calibration NFP is discarded, the regenerated NFP is not saved after being temporary used to measure authentication. The regenerated NFP is subsequently discarded for security reasons and the next regenerated NFP is generated and its match percentage with the authorized user calibration parameters evaluated. If the regenerated NFP is classified as having a match percentage greater than or equal to the access match level, access to the electronic device granted.

The training of the NFP authentication classifier may be linear or not (i.e., non-linear) depending upon the algorithm used by the classifier 1402.

To calibrate the classifier 1402, a predetermined value is selected for the calibration match percentage level. The predetermined value for the calibration match percentage level may be 100% or less. However, the predetermined value for the calibration match percentage level should be above the desired grant access match (AM) level.

Given the NFP calibration samples, the processor in the electronic device runs through test sequences of user calibration parameters in order to generate a match percentage equal to or greater than the predetermined value for the calibration match percentage level. Before selecting the initial user calibration parameters that generate a match percentage equal to or greater than the calibration match percentage level, the user may be asked to generate additional micro-motions (representing the NFP) by continuing to hold the device or continue to press the touch sensitive button. These additional NFPs are used to verify that the classifier is properly trained/calibrated by the user calibration parameters 1454.

After calibration, experiments were run to determine error rates in granting access to authorized users. Using a CEPSTRUM signal analysis of the micro-motions signal, a trained classifier in a hand held electronic device with accelerometer sensors had an error rate of 7% in recognizing the authorized user. An authorized user was correctly recognized 93% of the time. Accordingly, the access match (AM) level needs to be set below 93%, such as 80% for example, so that the authorized user is consistently authorized to access the electronic device.

When the CEPSTRUM signal analysis of the micro-motions signal was used with a touch sensitive keypad in an electronic device, error results seem to improve. When a small sample size of users typed their PIN number on a touch sensitive keypad, a one hundred percent recognition rate of the authorized user was achieved by the method using CESTRUM signal analysis. Regardless, the access match (AM) level needs to be set below 100%, such as 85% for example, so that the authorized user is consistently authorized to access the electronic device.

Alternatives to Cepstrum Signal Processing and Generating NFPs.

Many existing time-domain approaches to the task of signal classification are based on the existence of a fairly simple underlying pattern, or template, known a priori or learned from the data. With real signals however—like cardiac, speech, or electric motor systems—such a simple pattern rarely exists because of the complexity of the underlying processes. Indeed, frequency-based techniques are based on the existence of spectral patterns. From a stochastic processes perspective, frequency-based techniques of signal processing used on the micro-motions signal will just capture the first and second order characteristics of the system.

The CEPSTRUM analysis described herein can extract some time-related information from the accelerometer data, but this approach remains linked to the frequency dispersion. Because there is more information in the micro-motion signals than plain frequencies, other signal processing techniques and feature extraction methods may be able to improve the strength of an NFP so that it is less sensitive and less likely to change over time.

Chaos analytics may be used instead for example to generate NFPs. Using chaos, one could extract analogous predetermined features to that described with respect to the CEPSTRUM. However, these predetermine features are not based on frequencies, but with trajectories in time. Example features for extraction using Chaos analytics is the center of gravity of the strange attractor(s), combined with their fractal dimension, and Lyapunov exponent. Data sweeps over several seconds (e.g., 5, 10, 20 seconds) may be used to obtain values for these features from the micro-motions signal.

Another example of using chaos analytics is to use the waveform signal generated from the Logarithm of the spectrum for each axis without the IFT. From the logarithm waveform signal, amplitude and time can be taken as true coordinates of a vector and plotted for N (e.g., N=128) resolved frequencies at any given time. The centers, dimensionality and lyapunov, may be extracted as a time series of values representing the NFP.

In accordance with one embodiment, phase plots or Poincare plots (see Poincare plots 200A-200D shown in FIGS. 2A-2C for example) may be generated from which NFP signal features can be extracted and coupled into the NFP authentication classifier. There is more information in an orbit of a phase plot or Poincare plot than that of the Cepstrum waveforms. Accordingly, it is useful to use phase plots or Poincare plots, generated from the filtered micro-motions data-stream, from which to extract the features in the sensor data for an NFP.

In yet another embodiment, a hidden Markov model analysis is used as the signal processing module to obtain more feature information as the NFP to couple into the chosen classifier. A Markov model is a stochastic model used to model randomly changing systems where future states depend only on the present state and not on the sequence of events that preceded it. A Markov chain, a state space of one or more states, is often used as the Markov model. The transition from one state to another is a memory less random process. The next state depends only on the current state and not on the sequence of events that preceded it. A hidden Markov model is a Markov chain for which the state is only partially observable.

Figure 20:
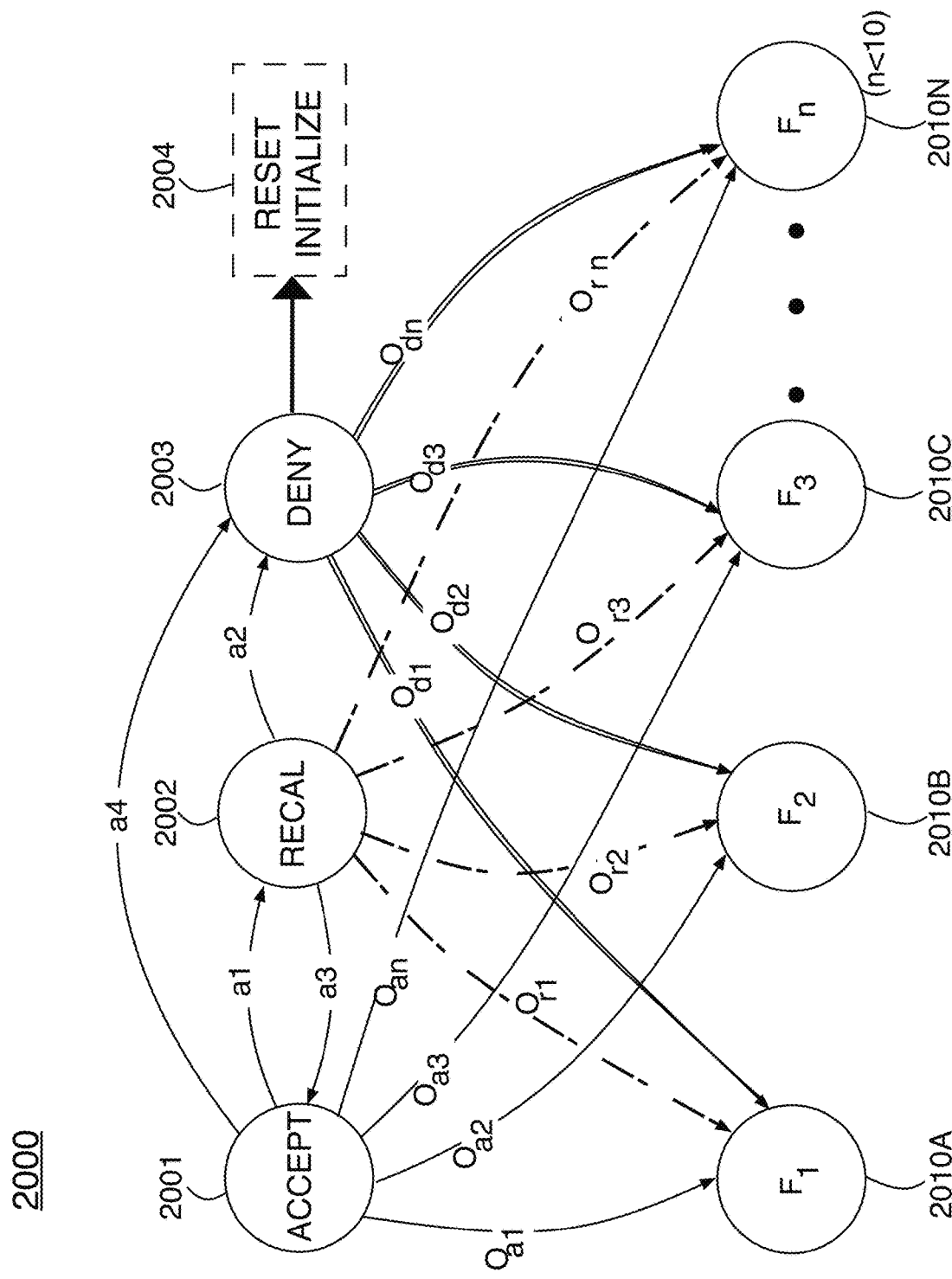
FIG. 20 illustrates a hidden Markov model that may be used as the NFP classifier model to determine a match percentage from an NFP and authorized user calibration parameters.

Referring now to FIG. 20, a state machine 2000 is illustrated that implements the hidden Markov model analysis. The state machine 2000 and hidden Markov model are used to extract features from a signal processed waveform of the micro-motions signal and perform the classification to grant or deny access (or authenticate a user).

The state machine 2000 includes states 2001-2004 and extracted features F1 2010A through Fn 2010N from a signal processes waveform (e.g., the Poincare plots shown in FIGS. 2A-2D) where N is less than or equal to 10. State 2001 is an accept state, state 2002 is a recalibration state, state 2003 is a deny state, and state 2004 is a reset/initialization state.

There are state transitions that can be made between the states 2001-2004 of the state machine 2000. State transition a1 is from the accept state 2001 to the recalibration state 2002. State transition a2 is from the recalibration state 2002 to the deny state 2003. State transition a3 is from the recalibration state 2002 to the accept state 2001. State transition a4 is from the accept state 2001 to the deny state 2003. The deny state 2003 may also transition to the reset/initialization state 2004.

From the states 2001-2003 to the features F1 2010A through Fn 2010N, there are output probabilities. From the accept state 2001 to the features F1 2010A through Fn 2010N, there are output probabilities Oa1 through Oan. From the recalibration state 2002 to the features F1 2010A through Fn 2010N, there are output probabilities Or1 through Orn. From the deny state 2003 to the features F1 2010A through Fn 2010N, there are output probabilities Od1 through Odn.

With a hidden Markov model, one tries to get at correct answers without having the inner details of the system that is being analyzed. The answers are the states 2001-2003, which are truly complex and based on chaotic inputs. The N features F1 2010A through Fn 2010N that are extracted are the only measurable. The features may be various, such as a center of gravity, or a series of Lyapunov exponents, whatever can be extracted out of data trajectories, each of which be related with specific odds ratios (e.g., Oa1-Oan, Or1-Orn, Od1-Odn) to the three states 2001-2003. One exits the state machine 2002 through the transition to the fourth state 2004. The fourth state 2004 corresponds to the system re-initialization, such as a full reset.

In still another embodiment, a dynamical systems signal analysis is performed based on reconstructed phase spaces (RPSs) with new signal classification approaches. Dynamical invariants may be used as the features that are to be extracted after the signal analysis. It is expected that this approach can capture more information leading to better user recognition.

Method of Use

As shown in FIGS. 8A-8C, a person holds the electronic device or touches one or more touch sensitive pads to authenticate himself/herself. For a few seconds of a sample period, a 3D sensor (3 sensors located on different axes) in the electronic device senses the vibrations or micro-motions in the user's hand or finger due to the physiological condition of the user's body. The 3D sensor generates three electronic signals concurrently in time that can be sampled and converted into digital form. The digital samples are preprocessed and analyzed using signal processing techniques to generate an NFP in real time for the user that just handled the electronic device or touched the touch sensor.

In response to authorized user calibration parameters, the NFP may then be used to evaluate whether or not the person holding or touching the electronic device is an authorized user. In response to authorized user calibration parameters, the NFP may be used as a key to encrypt and decrypt data files. Alternatively, a valid NFP may be used to authenticate a file was signed, written, or created by the authorized user.

The user calibration parameters may be stored in a local file or in a local storage device in the electronic device. Alternatively, the user calibration parameters may be stored in a remote file in a storage device associated with a server or in a storage device of a storage area network, in the internet cloud. The authorized user calibration parameters are useless without the hand or finger of the live authorized user. Without the hand or finger of the authorized user regenerating his/her NFP, access to the electronic device is denied.

Applications for NFP Authentication

The NFP Authentication system can be used to control access into an electronic device. The NFP authentication system may also be used to control access to functions associated with and software applications executed by the electronic device. The NFP authentication system can be used to control access to a remote electronic device (i.e., where the sensing is done on a local device to determine access to a remote electronic device.

Examples of functions that may have controlled access by the NFP authentication system include but are not limited to logons, user-protected accesses, e-transactions, and any other local function that requires positive authentication.

For example security applications for an NFP authentication system includes computer and software logins, electronic commerce, electronic banking, and anti-fraud applications. Examples of human control applications for an NFP authentication system include domotic authentication and protection (home security systems), car safety, and professional access to restricted zones. Examples of medical applications for an NFP authentication system include a diagnostic aid for health professionals (Neuromuscular a.o.), therapy monitoring for patients, and patient and doctor medical authentication (records, data routing, . . . ) into databases storing medical records. Examples of health and wellness applications for an NFP authentication system include securing physical fitness records of a user. Examples of gaming applications for an NFP authentication system include safety features for virtual reality gaming and/or simulators.

Biometric encryption combines touch recognition technology with the actual data storage. The data is encrypted with the NFP so that it is un-readable except by the authorized user/owner of the data. Backdoor access is unavailable. However, other authorized users that are trusted persons may also have authorized user calibration parameters generated so that they are granted access in case of problems related to the original user/owner.

Touch recognition technology can be embedded in certain applications. For example, touch recognition technology can be used in access control panels such that when a surface is touched by human hands or a human finger, a door may be unlocked so that access to a vehicle, a building (e.g., a home or office); or a zone (e.g., a floor) may be granted or denied in response to the user's NFP without using a key (keyless). Similarly, touch recognition technology can be used in a wireless key fob held in the user's hand or touched by a finger so that access may be granted or denied in response to the user's NFP without using a key. Touch recognition technology can be combined with fingerprint authentication. In this case, an image scanner and touch sensitive pad can be used together to concurrently capture both a user's fingerprint and the user's NFP for multiple authentications in granting or denying access.

With additional signal processing algorithms, the generation of the NFP may be adapted to monitor a user's health and wellness for health modifications. The change in the regeneration of the NFP can decrease the match percentage indicating a degradation in health of a user. On the other hand, an increase in the match percentage when the NFP is regenerated can indicate an improvement in the health and wellness of a user. It may be used to discover and/or monitor neurodegenerative diseases such as Alzheimer, Parkinson, or be used for therapeutic monitoring. It may be used to obtain measures of heart rhythm variability, the correlation of stress and emotional situations can be measured with accelerometers by extracting the shock waves of the cardiac pulses when a user holds a device. It may be used as a physiological safety feature for virtual reality glasses and goggles that may be used, such as in the video game industry.

As discussed previously with reference to FIG. 6, micro-motions and the micro-motions signals generated from the micro-motions may indicate a number of pathological conditions. A medical device employing touch technology/accelerometry and a controller can focus on analyzing the selected frequencies associated with these pathological conditions to determine health wellness or degradation. A medical device employing touch technology can also monitor the change in regeneration of an NFP over time to detect health and wellness changes. The change or drift in the NFP values between two or more time periods can be used as a way to monitor the health of a user.

The changes or drifts in NFP values can be qualified and/or quantified using one or more various analytical methods. One method of qualification and/or quantification of the drift would be to differentiate between intention tremors and resting tremors. Another such method would be a frequency or Fourier analysis. Yet another method may use chaos math-based classifiers to refine diagnosis. Still another method would be to perform comparisons of the same user at different times, such as in between doses of medications, or with and without medications, for example.

Furthermore, micro-motions and the micro-motions signals that are generated can vary when captured from different significant parts of the body (e.g., hands, limbs, rib cage) and even different sides of the body (e.g., left arm and right arm). The body tremors can differ when captured from different parts of the body. Monitoring the rib cage for body tremors may indicate hypothyroid conditions, fevers, or malignant hyperthermia conditions in the user. Monitoring the rib cage near the heart can achieve a measure of heart rhythm variability (HRV).

Figure 21:
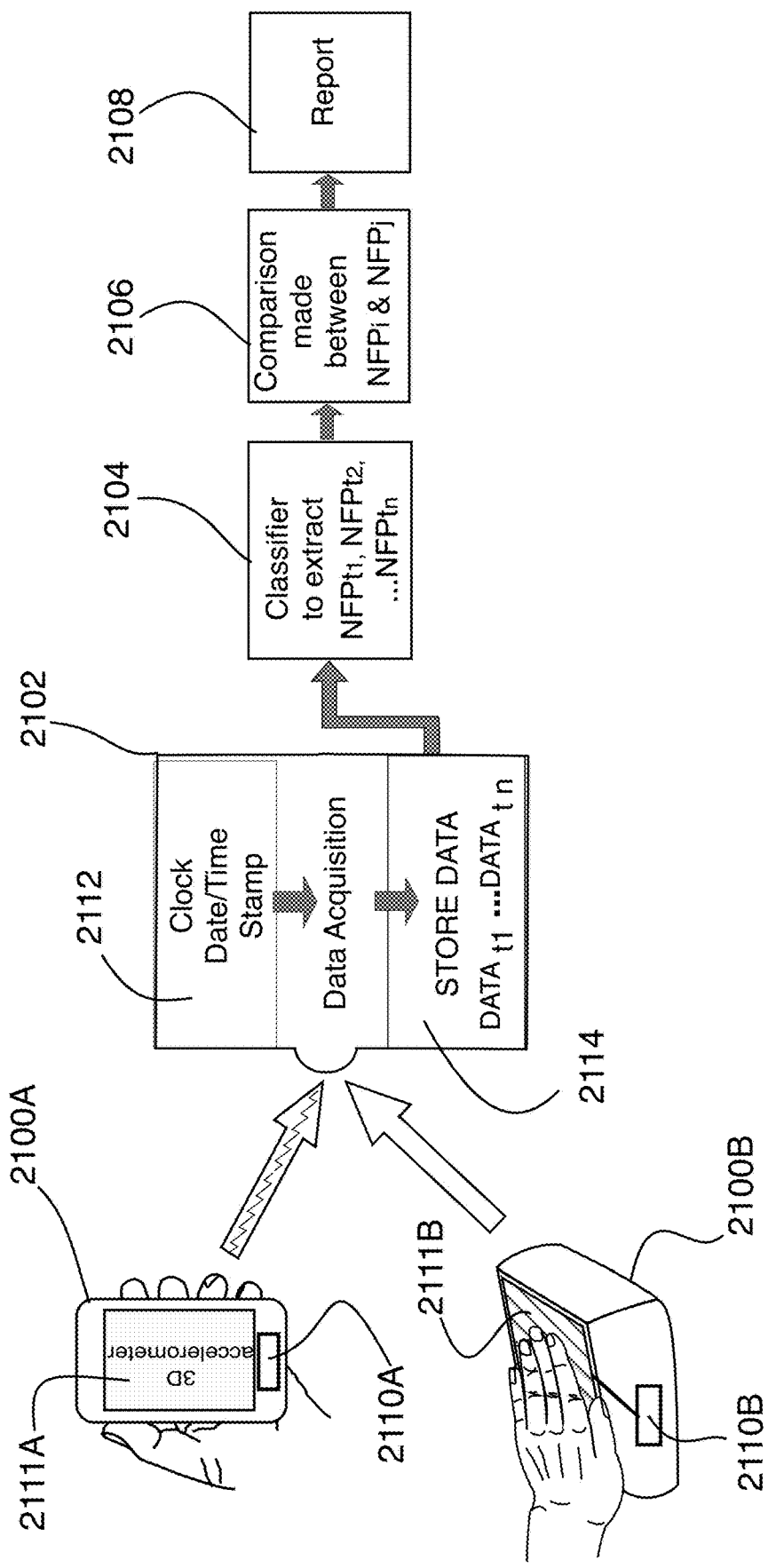
FIG. 21 illustrates a block diagram of a process for analyzing health of a user with neuro and neuro-mechanical fingerprints.

Referring now to FIG. 21, a pair of medical or health diagnostic devices 2100A-2100B are shown coupled in communication to a server 2102. The medical or health diagnostic devices 2100A-2100B may be located locally to the server using a local area communication network (LAN) for communication. Alternatively, the medical or health diagnostic devices 2100A-2100B may be located remotely from the server and communicate with the server over a wide area communication network (WAN), such as the Internet. The medical or health diagnostic devices 2100A-2100B may be held or touched by a user to sample micro-motions of the user. Alternatively, the medical or health diagnostic devices 2100A-2100B may be placed and/or strapped adjacent parts of the user's body (e.g., the chest) to capture micro-motions of the user at different areas and limbs of their body to perform different diagnostics. The medical or health diagnostic devices 2100A-2100B can include a user interface device (e.g., touch display 706, keypad 705, button 704, and/or audio speaker/microphone) and provide a user interface to instruct a user on how to use them for various types of diagnostic testing.

The medical or health diagnostic devices 2100A-2100B sample micro-motions of a user over time (different dates and time), generate and store micro-motions signals in response thereto for diagnosing changes in a user's health. The micro-motions signals that are captured are stored as data over time $DATA_{tm}$, with a date and time (date/time) stamp. A frequency analysis can be performed on one or more of stored micro-motions signals $DATA_{tm}$ to detect certain pathological conditions. The stored data $DATA_{tm}$ can also be analyzed to extract NFPs at each time stamp. A time analysis can be preformed comparing NFPs over date/time to detect changes between two or more NFPs. A report can then be generated explaining the frequency analysis of the stored micro-motions and the time analysis of NFPs over date/time.

The medical or health diagnostic device 2100A includes a controller 2110A and a three-dimensional accelerometer 2111A to sample micro-motions of the user and generate three-dimensional signals in response thereto on a given date and time. The medical or health diagnostic device 2100A may be wired or wirelessly in communication with server or other computer so that the three-dimensional signal from the medical or health diagnostic device 2100A can be uploaded to the server 2102. The kinematic motions of body parts of the user can be analyzed for micro-motions using the accelerometer 2111A.

The medical or health diagnostic device 2100B includes a controller 2110B and a multi-dimensional touch sensor 2111B of at least two dimensions to sample micro-motions of the user and generate multi-dimensional micro-motion signals (of at least two dimensions) in response thereto on a given date and time. The medical or health diagnostic device 2100B may be wired or wirelessly in communication with server or other computer so that the multi-dimensional signal can be uploaded to the server 2102.

In addition to one or more processors, the server 2102 includes a clock 2112 and a storage device 2114. The clock 2112 generates a date and time stamp that can be appended to the data representing the multi-dimensional micro-motions signal that is generated on the given time and date. The storage device 2114 stores a plurality of data, $DATA_{t1}$ through $DATA_{tn}$, representing the multi-dimensional micro-motions signals captured over time that is associated with the user/patient.

The server 2102 may further include a classifier 2104, a comparator 2106, and a report generator 2108. The classifier 2104, comparator 2106, and report generator 2108 may be a processor (e.g., processor 701 in FIG. 7) configured (in hardware, software, or a combination of hardware and software) by instructions.

The classifier 2104 may be a processor configured to perform one or more of the functional processes of the NFP authentication controller. The classifier 2104 generate NFPs from the plurality of data, $DATA_{t1}$ through $DATA_{tn}$, stored in the storage device 2114. That is, the stored data $DATA_{tn}$ is analyzed to extract $NFP_{tn}$ at each time stamp.

The comparator 2106 compares at least two NFPs, NFPi and NFPj, of different dates/times to detect changes between the two. If there is a negative difference between them over time that is greater than a predetermined percentage, it may indicate a degradation in health of the user. If there is a positive difference between them over time that is greater than a predetermined percentage, it may indicate an improvement in health of the user. The predetermined percentage may be set in response to the error tolerances of the system (e.g., 5%) measuring the NFPs.

The report generator 2108 generates the report that explains the frequency analysis of the stored micro-motions and the time analysis of NFPs over the dates/times. If a modification in health is detected, it is reported to the user. If the numbers are within the predetermined percentage, an indication that no health modification has been detected is reported to the user.

While the comparator 2106 analyzes the plurality of neuro-mechanical fingerprints over time, additional analysis can be performed by the system of device and server. The system can further analyze frequency components in each of the plurality of multi-dimensional motion signals in an attempt to determine a pathological condition that is a function of frequency. Moreover, the system can further search for one or more predetermined data patterns in multi-dimensional motion signals and/or neuro-mechanical fingerprints to determine a pathological condition that has a common data pattern or signature.

In addition to diagnosing health of a user, NFP technology can be used to protect medical records by better authentication of a patient and doctor, as well as encryption of the medical records. A user can authenticate his/her interactions with the health care system (providers, insurers, medical record companies, etc.). A user can securely store his/her medical records in the cloud or on any device in an encrypted format with the NFP being the key.

NFP technology can be used for online services. Governments may provide online services, such as voting, and the touch technology can be used to verify the identity of an authorized user. Schools and educators may provide online tests. Touch technology may be used to verify the identity of a user on a web page or web site portal where the user logs in. For example, a student taking an online test for example can be readily identified with NFP touch technology, even if the student takes a test at school. Electronic online banking can be made more secure with banks being able to verify the identity of its customers with the NFP touch technology.

Advantages of NFP Authentication

There are a number of advantages to touch recognition with a NFP. Touch recognition does not require a centralized database. Access to an electronic device is locally controlled and shielded by a local NFP user authentication system.

An additional advantage of NFP is that one can be uniquely identified as a proper user of an electronic device but remain anonymous, providing strong user privacy protection. The NFP is generated in response to brain/nerve system related signals generated by a sensor. It can provide next to foolproof unique user identification (even twins have different motricity).

Touch-recognition employs a neurological algorithm to generate an NFP from a micro-motion signal associated the micro motions of a finger on a hand. This avoids context-linked repertoires or motion repertoires that are associated with behavioral biometrics. It is user-friendly and can provide a friction-less login and authentication.

The neurological algorithms can be developed in software and added to pre-existing electronic devices with an application programming interface (API) or a mobile software development kit. It can be added as part of a system login.

The neurological algorithms need not continuously monitor a sensor. They can be sleeping until the electronic device is woken up from sleep or the sensor senses a touch. Training time and identification is quick, only a few seconds needed. Accordingly, the neurological algorithms can conserve power and intelligently use the battery power that is usually available in mobile device electronics.

CONCLUSION

When implemented in software, the elements of the embodiments are essentially the code segments of instructions that may be executed by one or more processors to perform and carry out tasks and provide functionality. For example, a processor (e.g., processor 701 in FIG. 7) may be configured (in hardware, software, or a combination of hardware and software) by instructions to perform the functional processes of the NFP authentication controller described herein. The program instructions or code segments can be stored in a processor readable medium or storage device (e.g., storage device 702 in FIG. 7) that are coupled to or at least in communication with the one or more processors. The processor readable medium may include a storage device or any medium that can store information. Examples of a processor readable medium include, but are not limited to, an electronic circuit, a semiconductor memory device, a read only memory (ROM), a flash memory, an erasable programmable read only memory (EPROM), a floppy diskette, a CD-ROM, an optical disk, a hard disk, or a solid state drive. The program or code segments may be downloaded or transmitted between storage devices, for example, over computer networks such as the Internet, Intranet, etc.

While this specification includes many specifics, these should not be construed as limitations on the scope of the disclosure or of what may be claimed, but rather as descriptions of features specific to particular implementations of the disclosure. Certain features that are described in this specification in the context of separate implementations may also be implemented in combination in a single implementation. Conversely, various features that are described in the context of a single implementation may also be implemented in multiple implementations, separately or in sub-combination. Moreover, although features may be described above as acting in certain combinations and even initially claimed as such, one or more features from a claimed combination may in some cases be excised from the combination, and the claimed combination may be directed to a sub-combination or variations of a sub-combination.

Accordingly, while certain exemplary embodiments have been particularly described and shown in the accompanying drawings, they should not be construed as limited by such embodiments, but rather construed according to the claims that follow below.

What is claimed is:

1. A method of determining a change in a user, the method comprising:
   under control of a processor
      sensing, with a multi-dimensional sensor, multi-dimensional motion of a body part at a plurality of dates/times;
      generating a plurality of multi-dimensional motion signals at the plurality of dates/times in response to the sensing;
      generating a plurality of neuro-mechanical fingerprints for the respective plurality of dates/times by extracting a plurality of predetermined features based on each of the plurality of multi-dimensional motion signals at each of the plurality of dates/times;
      comparing at least two of the plurality of neuro-mechanical fingerprints to determine a change in the user between at least two dates/times; and
      reporting the change to the user.

2. The method of claim 1, wherein
the comparing analyzes the plurality of neuro-mechanical fingerprints over time, and the method further comprises
analyzing frequency components in each of the plurality of multi-dimensional motion signals to determine a pathological condition of the user.

3. The method of claim 2, further comprises:
searching for one or more predetermined data patterns in each of the plurality of neuro-mechanical fingerprints to determine another pathological condition of the user.

4. The method of claim 1, further comprises:
searching for one or more predetermined data patterns in each of the plurality of neuro-mechanical fingerprints to determine a pathological condition of the user.

5. The method of claim 1, further comprises:
storing the plurality of multi-dimensional motion signals into a storage device for subsequent processing.

6. The method of claim 5, further comprises:
searching for one or more predetermined data patterns in each of the plurality of multi-dimensional motion signals to determine a pathological condition of the user.

7. A method of determining a change in a user, the method comprising:
   under control of a processor
      a) sensing multi-dimensional motion of a body part of a user to generate a first multi-dimensional motion signal at a first time and date;
      b) based on the first multi-dimensional motion signal, generating a first neuro-mechanical fingerprint (NFP) at the first time and date by extracting a plurality of predetermined features associated with the first multi-dimensional motion signal;
      c) generating a first measure based on the first NFP;
      d) sensing multi-dimensional motion of the body part of the user for consistency in order to generate another multi-dimensional motion signal at another time and date;
      e) based on the another multi-dimensional motion signal, generating another neuro-mechanical fingerprint (NFP) at the another time and date by extracting a plurality of predetermined features associated with the another multi-dimensional motion signal;
      f) generating another measure based on the another NFP; and
      g) comparing the first measure with the another measure to determine a difference between the first time and date and the another time and date, wherein the difference represents a change in the user.

8. The method of claim 7, further comprising
storing the first measure associated with the first time and date; and
storing the another measure associated with the another time and date.

9. The method of claim 7, further comprising
repeating steps d through g to continue determining the difference representing the change in the user.

10. The method of claim 9, wherein
the difference between the first measure and the another measure is positive.

11. The method of claim 9, wherein
the difference between the first measure and the another measure is negative.

12. The method of claim 11, wherein
the negative difference is associated with drinking alcohol; and the method further includes
restricting the user from operating machinery or a vehicle.

13. The method of claim 11, wherein
the negative difference is associated with a heart rhythm variability of the user and the method further includes
informing the user to see a doctor.

14. The method of claim 11, wherein
the negative difference is associated with a neurodegenerative disease of the user and the method further includes
informing the user to see a doctor.

15. The method of claim 14, wherein
the neurodegenerative disease is either Alzheimer's disease or Parkinson's disease.

16. The method of claim 7, wherein
the multi-dimensional motion of the body part of the user is sensed locally to generate the first multi-dimensional motion signal at a first time and date;
the first multi-dimensional motion signal is transmitted remotely over a communication system to a server to store the first multi-dimensional motion signal and generate a first neuro-mechanical fingerprint (NFP) in response thereto.

17. The method of claim 7, wherein
the multi-dimensional motion of the body part of the user is sensed in three dimensions with a three-dimensional touch sensor to generate a three dimensional motion signal at the first time and date.

18. The method of claim 7, wherein
the multi-dimensional motion of the body part of the user is sensed in three dimensions with a three-dimensional accelerometer to generate a three dimensional motion signal at the first time and date.

* * * * *